(12) United States Patent
Shashoua

(10) Patent No.: US 8,772,237 B2
(45) Date of Patent: *Jul. 8, 2014

(54) COMPOSITIONS AND METHODS FOR COUNTERACTING EFFECTS OF REACTIVE OXYGEN SPECIES AND FREE RADICALS

(75) Inventor: Victor E. Shashoua, Brookline, MA (US)

(73) Assignee: Ischemix, Inc.

( * ) Notice: Subject to any disclaimer, the term of this patent is extended or adjusted under 35 U.S.C. 154(b) by 174 days.

This patent is subject to a terminal disclaimer.

(21) Appl. No.: 13/218,685

(22) Filed: Aug. 26, 2011

(65) Prior Publication Data

US 2012/0058957 A1    Mar. 8, 2012

Related U.S. Application Data

(60) Division of application No. 11/986,456, filed on Nov. 21, 2007, now Pat. No. 8,034,774, which is a continuation of application No. 10/987,659, filed on Nov. 11, 2004, now abandoned, which is a division of application No. 09/715,763, filed on Nov. 17, 2000, now Pat. No. 6,890,896.

(60) Provisional application No. 60/166,381, filed on Nov. 18, 1999.

(51) Int. Cl.
*A61K 38/00* (2006.01)
*C07K 5/00* (2006.01)

(52) U.S. Cl.
USPC ............................................ 514/14; 530/300

(58) Field of Classification Search
None
See application file for complete search history.

(56) References Cited

U.S. PATENT DOCUMENTS

| | | | |
|---|---|---|---|
| 3,953,418 A | 4/1976 | Yanaihara et al. | |
| 4,277,464 A | 7/1981 | Reusiner et al. | |
| 4,297,344 A | 10/1981 | Schwinn et al. | |
| 4,783,441 A | 11/1988 | Thurow | |
| 4,812,557 A | 3/1989 | Yaushi et al. | |
| 5,096,885 A | 3/1992 | Pearlman et al. | |
| 5,098,893 A | 3/1992 | Franks et al. | |
| 5,112,870 A | 5/1992 | Mao et al. | |
| 5,242,901 A | 9/1993 | Speyer et al. | |
| 5,455,029 A | 10/1995 | Hartman et al. | |
| 5,538,878 A | 7/1996 | Thomas et al. | |
| 5,540,933 A | 7/1996 | Ruoslahti et al. | |
| 5,545,719 A | 8/1996 | Shashoua | |
| 5,559,095 A | 9/1996 | Miljanich et al. | |
| 5,766,857 A | 6/1998 | Ruoslahti et al. | |
| 5,804,427 A | 9/1998 | Davis et al. | |
| 5,962,634 A | 10/1999 | Jameson et al. | |
| 5,972,985 A | 10/1999 | Thomas et al. | |
| 5,981,478 A | 11/1999 | Ruoslahti et al. | |
| 6,174,862 B1 | 1/2001 | Brennemen | |
| 6,225,444 B1 | 5/2001 | Shashoua | |
| 6,242,577 B1 | 6/2001 | Ruoslahti et al. | |
| 6,469,049 B1 | 10/2002 | Meyerhoff et al. | |
| 6,613,887 B1 | 9/2003 | Ogi et al. | |
| 6,627,601 B2 | 9/2003 | Shashoua | |
| 6,645,501 B2 | 11/2003 | Dowdy | |
| 6,890,896 B1 * | 5/2005 | Shashoua | 514/5.5 |
| 7,524,819 B2 * | 4/2009 | Shashoua | 514/1.1 |
| 2001/0034035 A1 | 10/2001 | Shashoua | |
| 2005/0090446 A1 | 4/2005 | Shashoua | |
| 2006/0019901 A1 | 1/2006 | Shashoua | |

FOREIGN PATENT DOCUMENTS

| | | |
|---|---|---|
| EP | 0 488 979 A1 | 10/1991 |
| EP | 0 497 341 A2 | 5/1992 |
| EP | 0 567 886 A2 | 11/1993 |
| JP | 1294692 A | 11/1989 |
| JP | 9169797 A | 6/1997 |
| RU | 2099067 | 12/1997 |
| WO | WO 92/20362 A1 | 11/1992 |
| WO | WO 96/01643 A1 | 1/1996 |
| WO | WO 96/12505 A1 | 5/1996 |
| WO | WO 97/06815 A2 | 2/1997 |
| WO | WO 99/26620 A1 | 6/1999 |
| WO | WO 99/40112 A1 | 8/1999 |
| WO | WO 99/46823 A1 | 9/1999 |
| WO | WO 01/36454 A1 | 5/2001 |
| WO | WO 01/79272 A2 | 10/2001 |
| WO | WO 02/27016 A2 | 4/2002 |
| WO | WO 02/092781 A2 | 11/2002 |
| WO | WO 02/096360 A2 | 12/2002 |
| WO | WO 03/022226 A2 | 3/2003 |
| WO | WO 03/066814 A2 | 8/2003 |
| WO | WO 2006/101909 A2 | 9/2006 |
| WO | WO 2006/101910 A2 | 9/2006 |

OTHER PUBLICATIONS

Adams et al., Activation of a rel-A/CEBP-beta-related transcription factor heteromer by PGG-glucan in a murine monocytic cell line. J Cell Biochem. Mar. 2000;77(2):221-33.

Adams et al., Cloning and sequencing the genes encoding goldfish and carp ependymin. Gene. Apr. 20, 1994;141(2):237-41.

Adams et al., Genes encoding giant danio and golden shiner ependymin. Neurochem Res. Mar. 1996;21(3):377-84.

Adams et al., PGG-Glucan activates NF-kappaB-like and NF-IL-6-like transcription factor complexes in a murine monocytic cell line. J Leukoc Biol. Dec. 1997;62(6):865-73.

(Continued)

*Primary Examiner* — Anand Desai

(74) *Attorney, Agent, or Firm* — Wolf, Greenfield & Sacks, P.C.

(57) ABSTRACT

Peptide compounds and methods for upregulating expression of a gene encoding an antioxidative enzyme, such as superoxide dismutase or catalase, to counteract harmful oxidative effects of reactive oxygen species and other free radicals are described. The peptide compounds may be used to treat or prevent diseases and conditions characterized by undesirable elevation of reactive oxygen species and other free radicals, to upregulate AP-1 gene expression, and to treat pain. The peptide compounds may be used as components of pharmaceuticals and dietary supplements.

18 Claims, 6 Drawing Sheets

(56) References Cited

OTHER PUBLICATIONS

Adang et al., The glutathione-binding site in glutathione S-transferases. Investigation of the cysteinyl, glycyl and gamma-glutamyl domains. Biochem J. Jul. 1, 1990;269(1):47-54.

Altschul et al., Gapped BLAST and PSI-BLAST: a new generation of protein database search programs. Nucleic Acids Res. Sep. 1, 1997;25(17):3389-402. Review.

Angel et al., Phorbol ester-inducible genes contain a common cis element recognized by a TPA-modulated trans-acting factor. Cell. Jun. 19, 1987;49(6):729-39.

Bederson et al., Evaluation of 2,3,5-triphenyltetrazolium chloride as a stain for detection and quantification of experimental cerebral infarction in rats. Stroke. Nov.-Dec. 1986;17(6):1304-8.

Beyer et al., Assaying for superoxide dismutase activity: some large consequences of minor changes in conditions. Anal Biochem. Mar. 1987;161(2):559-66.

Bodansky and Bodansky, The Practice of Peptide Synthesis. New York: Springer Verlag, 1984.

Brenneman et al., Activity-dependent neurotrophic factor: structure-activity relationships of femtomolar-acting peptides. J Pharmacol Exp Ther. May 1998;285(2):619-27.

Büllesbach et al., Naturally occurring porcine relaxins and large-scale preparation of the B29 hormone. Biochemistry. Dec. 17, 1985;24(26):7717-22.

Carpenter et al., Rational design of stable lyophilized protein formulations: some practical advice. Pharm Res. Aug. 1997;14(8):969-75. Review.

Ceballos-Picot et al., [Transgenic mice overexpressing copper-zinc superoxide dismutase: a model for the study of radical mechanisms and aging] C R Seances Soc Biol Fil. 1993;187(3):308-23. Review. French.

Chan et al., Neuroprotective role of CuZn-superoxide dismutase in ischemic brain damage. Adv Neurol. 1996;71:271-280.

Cornell-Bell et al., Ca2+ waves in astrocytes. Cell Calcium. Feb.-Mar. 1991;12(2-3):185-204.

Cornell-Bell et al., Glutamate induces calcium waves in cultured astrocytes: long-range glial signaling. Science. Jan. 26, 1990;247(4941):470-3.

Del Arco et al., JNK (c-Jun NH2-terminal kinase) is a target for antioxidants in T lymphocytes. J Biol Chem. Oct. 18, 1996;271(42):26335-40.

Diamond et al., Reversing the amino acid sequence of a dipeptide changes its partition in an aqueous two-phase system. Biotechnology Techniques. 1989;3(4):271-274.

Diguiseppi et al., The toxicology of molecular oxygen. Crit Rev Toxicol. 1984;12(4):315-42. Review.

Erdincler et al., Lipid peroxidation and antioxidant status in experimental animals: effects of aging and hypercholesterolemic diet. Clin Chim Acta. Sep. 8, 1997;265(1):77-84.

Fischer et al., Possible role of free radical formation in clozapine (clozaril)-induced agranulocytosis. Mol Pharmacol. Nov. 1991;40(5):846-53.

Fridovich et al., Superoxide dismutases. Adv Enzymol Relat Areas Mol Biol. 1974;41(0):35-97. Review.

Gentry et al., Nerve growth factor activation of nuclear factor kappaB through its p75 receptor is an anti-apoptotic signal in RN22 schwannoma cells. J Biol Chem. Mar. 17, 2000;275(11):7558-65.

Gregorio-King et al., MERP1: a mammalian ependymin-related protein gene differentially expressed in hematopoietic cells. Gene. Mar. 20, 2002;286(2):249-57.

Halliwell, B. and Gutteridge, J.M.C., eds. Free Radicals in Biology and Medicine. Oxford: Clarendon Press, 1989.

Hanks et al., Relation of oxygen and temperature in the preservation of tissues by refrigeration. Proc Soc Exp Biol Med. Jun. 1949;71(2):196-200.

Horvitz et al., The genetics of programmed cell death in the nematode *Caenorhabditis elegans*. Cold Spring Harb Symp Quant Biol. 1994;59:377-85. Review.

Hsu et al., Expression of immediate early gene and growth factor mRNAs in a focal cerebral ischemia model in the rat. Stroke. Dec. 1993;24(12 Suppl):178-81.

Huang et al., [Leukogenic effect and antioxygen radicals function of fufang wuzi yanzong pills] Zhongguo Zhong Yao Za Zhi. Jul. 1991;16(7):414-6, 447. Chinese.

Jornot et al., Hyperoxia, unlike phorbol ester, induces glutathione peroxidase through a protein kinase C-independent mechanism. Biochem J. Aug. 15, 1997;326 ( Pt 1):117-23.

Kaiser et al., Color test for detection of free terminal amino groups in the solid-phase synthesis of peptides. Anal Biochem. Apr. 1970;34(2):595-8.

Lehninger A.L. Biochemistry. Second edition. New York: Worth Publishers, Inc. 1975; 72.

Leker et al., NAP, a femtomolar-acting peptide, protects the brain against ischemic injury by reducing apoptotic death. Stroke. Apr. 2002;33(4):1085-92.

Li et al., [Effects of wuzi yanzong pills on lipid in rats with alcohol-induced liver injury] Zhongguo Zhong Yao Za Zhi May 1994;19(5):300-2, inside backcover.

Li et al., Delayed triphenyltetrazolium chloride staining remains useful for evaluating cerebral infarct volume in a rat stroke model. J Cereb Blood Flow Metab. Oct. 1997;17(10):1132-5.

Longa et al., Reversible middle cerebral artery occlusion without craniectomy in rats. Stroke. Jan. 1989;20(1):84-91.

Longo et al., Synthetic NGF peptide derivatives prevent neuronal death via a p75 receptor-dependent mechanism. J Neurosci Res. Apr. 1, 1997;48(1):1-17.

Lucchesi et al., Myocardial ischemia, reperfusion and free radical injury. Am J Cardiol. May 22, 1990;65(19):14I-23I. Review.

Mecocci et al., Plasma antioxidants and longevity: a study on healthy centenarians. Free Radic Biol Med. Apr. 15, 2000;28(8):1243-8.

Meinwald et al., Deamidation of the asparaginyl-glycyl sequence. Int J Pept Protein Res. Jul. 1968;28(1):79-84. Erratum in: Int J Pept Protein Res Dec. 1986;28(6):following 660.

Melov et al., Extension of life-span with superoxide dismutase/catalase mimetics. Science. Sep. 1, 2000;289(5484):1567-9.

Merrifield et al., Solid phase peptide synthesis. I. The synthesis of a tetrapeptide. J Am Chem Soc. 1963;85:2149-2154.

Meyer et al., Regulation of the transcription factors NF-kappa B and AP-1 by redox changes. Chem Biol Interact. Jun. 1994;91(2-3):91-100.

Minematsu et al., Diffusion-weighted magnetic resonance imaging: rapid and quantitative detection of focal brain ischemia. Neurology. Jan. 1992;42(1):235-40.

Morgenstern et al., Identifying risk factors for tardive dyskinesia among long-term outpatients maintained with neuroleptic medications. Results of the Yale Tardive Dyskinesia Study. Arch Gen Psychiatry. Sep. 1993;50(9):723-33.

Murakami et al., Overexpression of CuZn-superoxide dismutase reduces hippocampal injury after global ischemia in transgenic mice. Stroke. Sep. 1997;28(9):1797-804.

Nagasawa et al., Correlation between cerebral blood flow and histologic changes in a new rat model of middle cerebral artery occlusion. Stroke. Aug. 1989;20(8):1037-43.

Niki et al., Oxidative stress and aging. Intern Med. Apr. 2000;39(4):324-6. Review.

Nimmrich et al., The novel ependymin related gene UCC1 is highly expressed in colorectal tumor cells. Cancer Lett. Apr. 10, 2001;165(1):71-9.

Orwar et al., Increased intra- and extracellular concentrations of gamma- glutamylglutamate and related dipeptides in the ischemic rat striatum: involvement of glutamyl transpeptidase. J Neurochem. Oct. 1994;63(4):1371-6.

Pahl et al., Oxygen and the control of gene expression. Bioessays. Jul. 1994;16(7):497-502. Review.

Pulsinelli et al., Regional cerebral blood flow and glucose metabolism following transient forebrain ischemia. Ann Neurol. May 1982;11(5):499-502.

Ratafia et al., Pharmaceutical Executive. 1991;74-80.

Reiter, Oxidative damage in the central nervous system: protection by melatonin. Prog Neurobiol. Oct. 1998;56(3):359-84.

(56) References Cited

OTHER PUBLICATIONS

Schäbitz et al., Intraventricular brain-derived neurotrophic factor reduces infarct size after focal cerebral ischemia in rats. J Cereb Blood Flow Metab. May 1997;17(5):500-6.

Shashoua et al., CMX-8933, a peptide fragment of the glycoprotein ependymin, promotes activation of AP-1 transcription factor in mouse neuroblastoma and rat cortical cell cultures. Neurosci Lett. Oct. 19, 2001;312(2):103-7.

Shashoua et al., Ependymin, a brain extracellular glycoprotein, and CNS plasticity. Ann N Y Acad Sci. 1991;627:94-114. Review.

Shashoua et al., Evidence for the in vivo polymerization of ependymin: a brain extracellular glycoprotein. Brain Res. Jul. 9, 1990;522(2):181-90.

Shashoua et al., N-docosahexaenoyl, 3 hydroxytyramine: a dopaminergic compound that penetrates the blood-brain barrier and suppresses appetite. Life Sci. 1996;58(16):1347-57.

Shashoua et al., Neuroprotective effects of a new synthetic peptide, CMX-9236, in in vitro and in vivo models of cerebral ischemia. Brain Res. Feb. 14, 2003;963(1-2):214-23.

Somani et al., Oxidants, Antioxidants, and Free Radicals. Chapter 6. Baskin, S.I. and H. Salem, eds. (Taylor &Francis, Washington, D.C., 1997).

Staatz et al., Identification of a tetrapeptide recognition sequence for the alpha 2 beta 1 integrin in collagen. J Biol Chem. Apr. 25, 1991;266(12):7363-7.

Suphioglu et al., Molecular cloning and immunological characterisation of Cyn d 7, a novel calcium-binding allergen from Bermuda grass pollen. FEBS Lett. Feb. 3, 1997;402(2-3):167-72.

Tabuchi et al., Rapid attenuation of AP-1 transcriptional factors associated with nitric oxide (NO)-mediated neuronal cell death. J Biol Chem. Dec. 6, 1996;271(49):31061-7.

Tang et al., Enhanced glial cell line-derived neurotrophic factor mRNA expression upon (−) -deprenyl and melatonin treatments. J Neurosci Res. Sep. 1, 1998;53(5):593-604.

Tong et al., Effect of nerve growth factor on AP-1, NF-kappa B, and Oct DNA binding activity in apoptotic PC12 cells: extrinsic and intrinsic elements. J Neurosci Res. Jul. 1, 1996;45(1):1-12.

Toyokuni et al., Reactive oxygen species-induced molecular damage and its application in pathology. Pathol Int. Feb. 1999;49(2):91-102. Review.

Tsai et al., Markers of glutamatergic neurotransmission and oxidative stress associated with tardive dyskinesia. Am J Psychiatry. Sep. 1998;155(9):1207-13.

Walton et al., Neuronal death and survival in two models of hypoxic-ischemic brain damage. Brain Res Brain Res Rev. Apr. 1999;29(2-3):137-68. Review.

Wang et al., [A clinical study of the effect of wuzi yanzong solution in retarding aging process] Zhongguo Zhong Xi Yi Jie He Za Zhi. Jan. 1992;12(1):23-5, 5. Chinese.

Wang et al., [Effect of wuzi yanzong liquid on hypothalamus, monoamines, sexual hormones and reproductivity in male rats] Zhongguo Zhong Xi Yi Jie He Za Zhi. Jun. 1993;13(6):349-51, 325-6, Chinese.

Wilkie et al., The non-peptidyl fungal metabolite L-783,281 activates TRK neurotrophin receptors. J Neurochem. Sep. 2001;78(5):1135-45.

Xie et al., Nerve growth factor (NGF) loop 4 dimeric mimetics activate ERK and AKT and promote NGF-like neurotrophic effects. J Biol Chem. Sep. 22, 2000;275(38):29868-74.

Yuan et al., The *C. elegans* cell death gene ced-3 encodes a protein similar to mammalian interleukin-1 beta-converting enzyme. Cell. Nov. 19, 1993;75(4):641-52.

Zamostiano et al., Cloning and characterization of the human activity-dependent neuroprotective protein. J Biol Chem. Jan. 5, 2001;276(1):708-14.

\* cited by examiner

SEQUENCE LISTING

<160> NUMBER OF SEQ ID NOS: 36

<210> SEQ ID NO 1
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1

Gln Tyr Lys Leu Gly Ser Lys Thr Gly Pro Gly Gln
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 2

Gln Thr Leu Gln Phe Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)...(1)
<223> OTHER INFORMATION: Xaa is Asp or Arg
<220> FEATURE:
<221> NAME/KEY: misc_feature
<222> LOCATION: (3)...(3)
<223> OTHER INFORMATION: Xaa is Asp or Arg
<220> FEATURE:
<221> NAME/KEY: misc_feature
<222> LOCATION: (4)...(4)
<223> OTHER INFORMATION: Xaa is absent or Gly
<220> FEATURE:
<221> NAME/KEY: misc_feature
<222> LOCATION: (5)...(5)
<223> OTHER INFORMATION: Xaa is absent, Asp or Phe
<220> FEATURE:
<221> NAME/KEY: misc_feature
<222> LOCATION: (6)...(6)
<223> OTHER INFORMATION: Xaa is absent, Ala or Phe
<220> FEATURE:
<221> NAME/KEY: misc_feature
<222> LOCATION: (7)...(7)
<223> OTHER INFORMATION: Xaa is absent or Ala

<400> SEQUENCE: 3

Xaa Gly Xaa Xaa Xaa Xaa Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 4

Asp Gly Asp Gly Asp
1               5

```
<210> SEQ ID NO 5
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 5

Asp Gly Asp Gly Phe Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 6

Asp Gly Asp Gly Asp Phe Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 7

Asp Gly Asn Gly Asp Phe Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 8

Asn Gly Asn Gly Asp Phe Ala
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 9

Asn Gly Asp Gly Asp Phe Ala
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)...(1)
<223> OTHER INFORMATION: Xaa is absent or Ser
<220> FEATURE:
<221> NAME/KEY: misc_feature
<222> LOCATION: (2)...(2)
<223> OTHER INFORMATION: Xaa is absent or Lys
```

<400> SEQUENCE: 10

Xaa Xaa Met Thr Leu Thr Gln Pro
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 11

Met Thr Leu Thr Gln Pro
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 12

Ser Lys Met Thr Leu Thr Gln Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 13

Glu Thr Leu Gln Phe Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 14

Gln Tyr Ser Ile Gly Gly Pro Gln
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 15

Ser Asp Arg Ser Ala Arg Ser Tyr
1               5

<210> SEQ ID NO 16
<211> LENGTH: 12
<212> TYPE: PRT
<213> ORGANISM: Artificial Sequence
<220> FEATURE:
<223> OTHER INFORMATION: Synthetic Polypeptide

```
<400> SEQUENCE: 16

Asp Gly Asp Gly Asp Phe Ala Ile Asp Ala Pro Glu
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 17

Asn Gly Asn Gly Asp
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 18

Asp Gly Asn Gly Asp
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 19

Asn Gly Asp Gly Asp
1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 20

Asn Gly Asp Gly
1

<210> SEQ ID NO 21
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 21

Asn Gly Asn Gly Phe Ala
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 22
```

```
Asp Gly Asn Gly Phe Ala
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 23

Asn Gly Asp Gly Phe Ala
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 24

Lys Lys Glu Thr Leu Gln Phe Arg
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 25

Lys Lys Gln Thr Leu Gln Phe Arg
1               5

<210> SEQ ID NO 26
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 26

Lys Lys Asp Gly Asp Gly Asp Phe Ala Ile Asp Ala Pro Glu
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 27

Lys Lys Gln Tyr Lys Leu Gly Ser Lys Thr Gly Pro Gly Gln
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 28
```

Lys Lys Asp Gly Asp Gly Asp Phe Ala
1               5

<210> SEQ ID NO 29
<211> LENGTH: 25
<212> TYPE: DNA
<213> ORGANISM: Artificial Sequence
<220> FEATURE:
<223> OTHER INFORMATION: Primer Sequence

<400> SEQUENCE: 29
atcccaatca ctccacaggc caagc					25

<210> SEQ ID NO 30
<211> LENGTH: 25
<212> TYPE: DNA
<213> ORGANISM: Artificial Sequence
<220> FEATURE:
<223> OTHER INFORMATION: Primer Sequence

<400> SEQUENCE: 30
gagacctggg caatgtgact gctgg					25

<210> SEQ ID NO 31
<211> LENGTH: 25
<212> TYPE: DNA
<213> ORGANISM: Artificial Sequence
<220> FEATURE:
<223> OTHER INFORMATION: Primer Sequence

<400> SEQUENCE: 31
gcccgagtcc aggctcttct ggacc					25

<210> SEQ ID NO 32
<211> LENGTH: 25
<212> TYPE: DNA
<213> ORGANISM: Artificial Sequence
<220> FEATURE:
<223> OTHER INFORMATION: Primer Sequence

<400> SEQUENCE: 32
ttggcagcta tgtgagagcc ggcct					25

<210> SEQ ID NO 33
<211> LENGTH: 21
<212> TYPE: DNA
<213> ORGANISM: Artificial Sequence
<220> FEATURE:
<223> OTHER INFORMATION: Primer Sequence

<400> SEQUENCE: 33
cgcttgatga ctcagccgga a						21

<210> SEQ ID NO 34
<211> LENGTH: 21
<212> TYPE: DNA
<213> ORGANISM: Artificial Sequence
<220> FEATURE:
<223> OTHER INFORMATION: Primer Sequence

<400> SEQUENCE: 34
cgcttgatga cttggccgga a						21

<210> SEQ ID NO 35
<211> LENGTH: 21
<212> TYPE: DNA

```
<213> ORGANISM: Artificial Sequence
<220> FEATURE:
<223> OTHER INFORMATION: Primer Sequence

<400> SEQUENCE: 35
cgcttgatga gtcagccgga a                                              21

<210> SEQ ID NO 36
<211> LENGTH: 21
<212> TYPE: DNA
<213> ORGANISM: Artificial Sequence
<220> FEATURE:
<223> OTHER INFORMATION: Primer Sequence

<400> SEQUENCE: 36
cgcttgatga gttggccgga a                                              21
```

COMPOSITIONS AND METHODS FOR COUNTERACTING EFFECTS OF REACTIVE OXYGEN SPECIES AND FREE RADICALS

RELATED APPLICATIONS

This application is a divisional of Ser. No. 11/986,456, filed Nov. 21, 2007, now U.S. Pat. No. 8,034,774, which is a continuation of Ser. No. 10/987,659 filed Nov. 11, 2004, now abandoned; which is a divisional of Ser. No. 09/715,763 filed Nov. 17, 2000, now U.S. Pat. No. 6,890,896; which claims the benefit under 35 U.S.C. 119 to U.S. provisional patent application Ser. No. 60/166,381, filed Nov. 18, 1999, each of which are hereby incorporated by reference herein in their entirety.

FIELD OF THE INVENTION

The present invention is in the field of antioxidative compounds, in particular, pharmaceutical and nutraceutical compounds for use in therapeutic and prophylactic treatments of diseases and conditions characterized by undesirable levels of reactive oxygen species and free radicals.

BACKGROUND TO THE INVENTION

Biological organisms generate harmful reactive oxygen species (ROS) and various free radicals in the course of normal metabolic activities of tissues such as brain, heart, lung, and muscle tissue (Halliwell, B. and Gutteridge, J. M. C., eds. *Free Radicals in Biology and Medicine*, (Oxford: Clarendon Press, 1989)). The most reactive and, therefore, toxic ROS and free radicals include the superoxide anion ($O_2.^-$), singlet oxygen, hydrogen peroxide ($H_2O_2$), lipid peroxides, peroxinitrite, and hydroxyl radicals. Even a relatively small elevation in ROS or free radical levels in a cell can be damaging. Likewise, a release or increase of ROS or free radicals in extracellular fluid can jeopardize the surrounding tissue and result in tissue destruction and necrosis. Indeed, hydrogen peroxide, which is somewhat less reactive than the superoxide anion, is a well known, broad spectrum, antiseptic compound. In eukaryotes, a major source of superoxide anion is the electron transport system during respiration in the mitochondria. The majority of the superoxide anion is generated at the two main sites of accumulation of reducing equivalents, i.e., the ubiquinone-mediated and the NADH dehydrogenase-mediated steps in the electron transport mechanism. Hydrogen peroxide is generated metabolically in the endoplasmic reticulum, in metal-catalyzed oxidations in peroxisomes, in oxidative phosphorylation in mitochondria, and in the cytosolic oxidation of xanthine (see, for example, Somani et al., "Response of Antioxidant System to Physical and Chemical Stress," In *Oxidants, Antioxidants, and Free Radicals*, chapter 6, pp. 125-141, Baskin, S. I. and H. Salem, eds. (Taylor & Francis, Washington, D.C., 1997)).

In normal and healthy individuals, several naturally occurring antioxidant defense systems detoxify the various ROS or free radicals and, thereby, preserve normal cell and tissue integrity and function. These systems of detoxification involve the stepwise conversion of ROS or free radicals to less toxic species by the concerted activities of certain antioxidative enzymes. These antioxidative enzymes are members of a larger class of molecules known as "oxygen radical scavengers" or "lazaroids" that have an ability to scavenge and detoxify ROS and free radicals. Vitamins A, C, E, and related antioxidant compounds, such as β-carotene and retinoids, are also members of this larger class. In healthy individuals, sufficient levels of antioxidative enzymes and other lazaroids are present both intracellularly and extracellularly to efficiently scavenge sufficient amounts of ROS and free radicals to avoid significant oxidative damage to cells and tissues.

Superoxide dismutase (SOD), catalase (CAT) and glutathione peroxidase (GSH-Px) are among the most important and studied of the antioxidative enzymes. These enzymes function in concert to detoxify ROS and free radicals. SOD is present in virtually all oxygen-respiring organisms where its major function is the dismutation (breakdown) of superoxide anion to hydrogen peroxide. Hydrogen peroxide, itself, is a highly reactive and oxidative molecule, which must be further reduced to avoid damage to cells and tissues. In the presence of the appropriate electron acceptors (hydrogen donors), CAT catalyzes the further reduction of hydrogen peroxide to water. In the presence of reduced glutathione (GSH), GSH-Px also mediates reduction of hydrogen peroxide to water by a separate pathway.

Each of the antioxidative enzymes described above can be further subdivided into classes. There are three distinct classes of SOD based on metal ion content: copper-zinc (Cu—Zn), manganese (Mn), and iron (Fe). In mammals, only the Cu—Zn and Mn SOD classes are present. Mammalian tissues contain a cytosolic Cu—Zn SOD, a mitochondrial Mn SOD, and a Cu—Zn SOD referred to as EC-SOD, which is secreted into the extracellular fluid. SOD is able to catalyze the dismutation of the highly toxic superoxide anion at a rate of 10 million times faster than the spontaneous rate (see, Somani et al., p. 126). Although present in virtually all mammalian cells, the highest levels of SOD activity are found in several major organs of high metabolic activity, i.e., liver, kidney, heart, and lung. Expression of the gene encoding SOD has been correlated with tissue oxygenation; high oxygen tension elevates SOD biosynthesis in rats (Toyokuni, S., *Pathol. Int.*, 49: 91-102 (1999)).

CAT is a soluble enzyme present in nearly all mammalian cells, although CAT levels can vary widely between tissues and intracellular locations. CAT is present predominately in the peroxisomes (microbodies) in liver and kidney cells and also in the microperoxisomes of other tissues.

There are two distinct classes of GSH-Px: selenium-dependent and selenium independent. Furthermore, GSH-Px species can be found in the cytosol, as a membrane-associated protein, and as a circulating plasma protein.

A recognition of the role of ROS and free radicals in a variety of important diseases and drug side effects has grown appreciably over recent years. Many studies have demonstrated that a large number of disease states and harmful side effects of therapeutic drugs are linked with a failure of the antioxidant defense system of an individual to keep up with the rate of generation of ROS and various free radicals (see, for example, Chan et al., *Adv. Neurol.*, 71:271-279 (1996); DiGuiseppi, J. and Fridovich, I., *Crit. Rev. Toxicol.*, 12:315-342 (1984)). For example, abnormally high ROS levels have been found under conditions of anoxia elicited by ischemia during a stroke or anoxia generated in heart muscle during myocardial infarction (see, for example, Walton, M. et al., *Brain Res. Rev.*, 29:137-168 (1999); Pulsinelli, W. A. et al., *Ann. Neurol.*, 11: 499-502 (1982); Lucchesi, B. R., *Am. J. Cardiol.*, 65:14I-23I (1990)). In addition, an elevation of ROS and free radicals has also been linked with reperfusion damage after renal transplants. Accordingly, an elevation of ROS and free radicals has been linked with the progression and complications developed in many diseases, drug treatments, traumas, and degenerative conditions including oxidative stress induced damage with age, Tardive dyskinesia, Parkinson's disease, Huntington's disease, degenerative eye diseases, septic shock, head and spinal cord injuries, Alzheimer's disease, ulcerative colitis, human leukemia and other cancers, and diabetes (see, for example, Ratanis, *Pharmaceutical Executive*, pp. 74-80 (April 1991)).

One approach to reducing elevated levels of damaging ROS and free radicals has involved an attempt to increase the levels of antioxidative enzymes and other lazaroids by administering those agents therapeutically. As a result, the commercial market for antioxidative enzymes and other lazaroids is estimated to exceed $1 billion worldwide. Not surprisingly, research and development of various lazaroids as therapeutic agents has become a highly competitive field. Interest in developing SOD itself as a therapeutic agent has been especially strong. This is due, in part, to SOD's status as a recognized anti-inflammatory agent and the belief that SOD might provide a means for penetrating the nonsteroidal, anti-inflammatory drug (NSAID) market as well (Id., at p. 74).

Despite many years of focused research effort, the use of SOD and other lazaroids has not provided a successful prophylactic or therapeutic tool for addressing the diseases, disorders and other conditions caused by or characterized by the generation of ROS and free radicals. Clearly, there remains a need for additional therapeutics and methods of treating diseases and conditions characterized by the destructive effect of elevated levels of ROS and free radicals.

SUMMARY OF THE INVENTION

The invention described herein solves the problem of how to counteract the destructive oxidative effect of elevated levels of ROS and free radicals by providing peptide compounds that stimulate (i.e., upregulate) expression of genes encoding antioxidative enzymes, such as superoxide dismutase (SOD) and/or catalase (CAT), to reduce, eliminate, or prevent an undesirable elevation in the levels of ROS and free radicals in cells and tissues, and to restore age-related reduction of constitutive antioxidative enzymes. Furthermore, the peptide compounds of this invention may have antioxidative activity independent of their ability to stimulate expression of genes encoding antioxidative enzymes. The formulas of the peptide compounds described herein use the standard three-letter abbreviation for amino acids known in the art.

In one embodiment, the invention provides a peptide compound having the formula:

(SEQ ID NO: 1)
$R_1$ Gln Tyr Lys Leu Gly Ser Lys Thr Gly Pro Gly Gln $R_2$, wherein $R_1$ is absent or is an amino terminal capping group and $R_2$ is absent or is a carboxy terminal capping group of the peptide compound and wherein the peptide compound upregulates expression of a gene encoding an antioxidative enzyme.

In another embodiment, the invention provides a peptide compound having the formula:

$R_1$ Gln Thr Leu Gln Phe Arg $R_2$,   (SEQ ID NO: 2)

wherein $R_1$ is absent or is an amino terminal capping group and $R_2$ is absent or is a carboxy terminal capping group of the peptide compound and wherein the peptide compound upregulates expression of a gene encoding an antioxidative enzyme.

In yet another embodiment, the invention provides a peptide compound having the formula:

(SEQ ID NO: 3)
$R_1$ $Xaa_1$ Gly $Xaa_2$ $Xaa_3$ $Xaa_4$ $Xaa_5$ $Xaa_6$ $R_2$, wherein $Xaa_1$ and $Xaa_2$ are, independently, aspartic acid or asparagine; $R_1$ is absent or is an amino terminal capping group of the peptide compound; $Xaa_3$ is absent or Gly; $Xaa_4$ is absent, Asp, or Phe; $Xaa_5$ is absent, Ala, or Phe; $Xaa_6$ is absent or Ala; $R_2$ is absent or is a carboxy terminal capping group of the peptide compound; and wherein the peptide compound upregulates expression of a gene encoding an antioxidative enzyme. A preferred peptide compound according to the formula, upregulates expression of a gene encoding an antioxidative enzyme and comprises an amino acid sequence selected from the group consisting of:

Asp Gly Asp

Asp Gly Asn

Asn Gly Asn

Asn Gly Asp

Asp Gly Asp Gly Asp,           (SEQ ID NO: 4)

Asp Gly Asp Gly Phe Ala,       (SEQ ID NO: 5)

Asp Gly Asp Gly Asp Phe Ala,   (SEQ ID NO: 6)

Asp Gly Asn Gly Asp Phe Ala,   (SEQ ID NO: 7)

Asn Gly Asn Gly Asp Phe Ala,   (SEQ ID NO: 8)
and

Asn Gly Asp Gly Asp Phe Ala.   (SEQ ID NO: 9)

The invention also provides a peptide compound having the formula:

$R_1$ Asn Ser Thr $R_2$, wherein $R_1$ is absent or is an amino terminal capping group; $R_2$ is absent or is a carboxy terminal capping group of the peptide compound; and wherein the peptide compound upregulates expression of a gene encoding an antioxidative enzyme.

In still another embodiment, the invention provides a peptide compound having the formula:

$R_1$PheAspGln$R_2$, wherein $R_1$ is absent or is an amino terminal capping group; $R_2$ is absent or is a carboxy terminal capping group of the peptide compound; and wherein the peptide compound upregulates expression of a gene encoding an antioxidative enzyme.

In another embodiment, the invention provides a peptide compound having the formula:

(SEQ ID NO: 10)
$R_1$ $Xaa_1$ $Xaa_2$ Met Thr Leu Thr Gln Pro $R_2$, wherein $Xaa_1$ is absent or Ser; $Xaa_2$ is absent or Lys; $R_1$ is absent or is an amino terminal capping group; $R_2$ is absent or is a carboxy terminal capping group of the peptide compound; and wherein the peptide compound upregulates expression of a gene encoding an antioxidative enzyme. A preferred peptide compound according to the formula, upregulates expression of a gene encoding an antioxidative enzyme and comprises an amino acid sequence selected from the group consisting of:

```
Met Thr Leu Thr Gln Pro         (SEQ ID NO: 11)
and
Ser Lys Met Thr Leu Thr Gln Pro  (SEQ ID NO: 12)
```

The invention also provides a peptide compound having the formula:

$$R_1Xaa_1Xaa_2Xaa_3R_2,$$

wherein $Xaa_1$ is Asp, Asn, Glu, Gln, Thr, or Tyr; $Xaa_2$ is absent or any amino acid (i.e., is variable); $Xaa_3$ is Asp, Asn, Glu, Thr, Ser, Gly, or Leu; $R_1$ is absent or is an amino terminal capping group and $R_2$ is absent or is a carboxy terminal capping group of the peptide compound; wherein the peptide compound upregulates expression of a gene encoding an antioxidative enzyme. Preferably, a peptide compound of the invention comprises the above formula wherein $Xaa_2$ is selected from the group consisting of Val, Gly, Glu, and Gln. More preferably, the peptide compound is selected from the group consisting of:

Asp Gly, Asn Gly, Glu Gly, Gln Gly, Thr Val Ser, Asp Gly Asp, and ASn Gly Asn.

In still another embodiment, the invention provides a peptide compound having the formula:

$$R_1LeuXaa_1Xaa_2R_2,$$

wherein $Xaa_1$ is any amino acid; $Xaa_2$ is Gln or Tyr; $R_1$ is absent or is an amino terminal capping group; $R_2$ is absent or is a carboxy terminal capping group of the peptide compound; and wherein the peptide compound upregulates expression of a gene encoding an antioxidative enzyme.

The invention also provides a peptide compound having the formula:

$$R_1MetThrXaa_1R_2,$$

wherein $Xaa_1$ is Asn, Asp, Glu, Thr, or Leu; $R_1$ is absent or is an amino terminal capping group; $R_2$ is absent or is a carboxy terminal capping group of the peptide compound; and wherein the peptide compound upregulates expression of a gene encoding an antioxidative enzyme.

In a preferred embodiment, a peptide compound of any of the formulas described herein has the $R_1$ amino terminal capping group. More preferably, the $R_1$ amino terminal capping group is selected from the group consisting of a lipoic acid moiety (Lip, in reduced or oxidized form); a glucose-3-O-glycolic acid moiety (Gga); 1 to 6 lysine residues; 1 to 6 arginine residues; an acyl group of the formula $R_3$—CO—, where CO is a carbonyl group, and $R_3$ is a hydrocarbon chain having from 1 to 25 carbon atoms, and preferably 1 to 22 carbon atoms, and where the hydrocarbon chain may be saturated or unsaturated and branched or unbranched; and combinations thereof. More preferably, when the amino terminal capping group is an acyl group it is acetyl or a fatty acid. Even more preferably, the amino terminal capping group is an acyl group selected from the group consisting of acetyl, palmitic acid (Palm), and docosahexaenoic acid (DHA). In another embodiment, the amino terminal capping group is a peptide consisting of any combination of arginine and lysine wherein the peptide is not less than two amino acids in length and not more than six amino acids in length.

Preferred peptide compounds that upregulate expression of a gene encoding an antioxidative enzyme and that are useful in compositions and methods of the invention include, but are not limited to, those peptides comprising an amino acid sequence selected from the group consisting of:

```
                                       (SEQ ID NO: 1)
Gln Tyr Lys Leu Gly Ser Lys Thr Gly Pro Gly Gln, (SEQ ID NO: 2)
Gln Thr Leu Gln Phe Arg, (SEQ ID NO: 13)
Glu Thr Leu Gln Phe Arg, (SEQ ID NO: 14)
Gln Tyr Ser Ile Gly Gly Pro Gln, (SEQ ID NO: 15)
Ser Asp Arg Ser Ala Arg Ser Tyr, (SEQ ID NO: 12)
Ser Lys Met Thr Leu Thr Gln Pro, (SEQ ID NO: 13)
Met Thr Leu Thr Gln Pro, (SEQ ID NO: 16)
Asp Gly Asp Gly Asp Phe Ala Ile Asp Ala Pro Glu, (SEQ ID NO: 6)
Asp Gly Asp Gly Asp Phe Ala, (SEQ ID NO: 4)
Asp Gly Asp Gly Asp, (SEQ ID NO: 8)
Asn Gly Asn Gly Asp Phe Ala, (SEQ ID NO: 17)
Asn Gly Asn Gly Asp, (SEQ ID NO: 7)
Asp Gly Asn Gly Asp Phe Ala, (SEQ ID NO: 18)
Asp Gly Asn Gly Asp, (SEQ ID NO: 9)
Asn Gly Asp Gly Asp Phe Ala, (SEQ ID NO: 19)
Asn Gly Asp Gly Asp, (SEQ ID NO: 20)
Asn Gly Asp Gly, (SEQ ID NO: 5)
Asp Gly Asp Gly Phe Ala, (SEQ ID NO: 21)
Asn Gly Asn Gly Phe Ala, (SEQ ID NO: 22)
Asp Gly Asn Gly Phe Ala, (SEQ ID NO: 23)
Asn Gly Asp Gly Phe Ala,
```

Asp Gly Asp, Asn Gly Asn, Asp Gly Asn, Asn Gly Asp, Asn Ser Thr, Phe Asp Gln, Met Thr Leu, Met Thr Asp, Met Thr Asn, Met Thr Thr, Met Thr Glu, Met Thr Gln, Thr Val Ser, Leu Thr Gln, Leu Thr Gly, Leu Thr Tyr, Asp Gly, Asn Gly, Glu Gly, Gln Gly, Glu Ala, Gln Ala, Gln Gly, Asp Ala, and Asn Ala.

Even more preferred peptide compounds that are useful in compositions and methods of the invention comprise an amino acid sequence selected from the group consisting of Asp Gly Asp, Asp Gly, Thr Val Ser, and Glu Ala.

In a more preferred embodiment, the invention provides the above-listed preferred peptide compounds that also have an amino terminal capping group and/or a carboxy terminal capping group. Even more preferred, the amino terminal capping group is selected from a group consisting of a reduced or oxidized lipoic acid moiety (Lip), a glucose-3-O-glycolic acid (Gga) moiety, 1 to 6 lysine residues, 1 to 6 arginine residues, an acyl group having the formula $R_3$—CO—, where CO represents a carbonyl group and $R_3$ is a saturated or an unsaturated (mono- or polyunsaturated) hydrocarbon chain having from 1 to 25 carbons, and combinations thereof. Still more preferably, the amino terminal capping group is the $R_3$—CO— acyl group wherein $R_3$ is a saturated or unsaturated hydrocarbon chain having Ito 22 carbons. Even more preferably, the amino terminal capping group is the acyl group that is an acetyl group (Ac), palmitic acid (Palm), or docosahexaenoic acid (DHA). In another preferred embodiment, the above-listed preferred peptide compounds have a carboxy terminal capping group selected from the group consisting of a primary or secondary amine.

The peptide compounds useful in the compositions and/or methods of the invention may also be prepared and used as one or more various salt forms, including acetate salts and trifluoroacetic acid salts, depending on the needs for a particular composition or method.

The invention also provides methods of counteracting the effects of ROS and free radicals in cells and tissues comprising contacting the cells or tissues with a peptide compound described herein. In a preferred embodiment of the invention, the peptide compounds of the invention stimulate (upregulate) expression of a gene(s) encoding superoxide dismutase (SOD) and/or catalase (CAT) enzymes, which enzymes are capable of detoxifying ROS and free radicals in cells and tissues of animals, including humans and other mammals. Preferably, gene expression for both SOD and CAT proteins are upregulated by contacting cells or tissues with a peptide compound of this invention. Treating cells or tissues with a peptide compound described herein may elevate the expression of gene(s) encoding SOD and/or CAT to sufficiently high levels to provide significantly increased detoxification of ROS and free radicals compared to untreated cells or tissues.

Patients having a variety of diseases or conditions have been found to possess undesirable levels of ROS and/or free radicals. In a preferred embodiment of the invention, a composition comprising a peptide compound described herein may be used therapeutically to counteract the effects of ROS and free radicals present in the body and/or prophylactically to decrease or prevent an undesirable elevation in the levels of ROS and free radicals associated with particular diseases, conditions, drug treatments, or disorders. Specifically, this invention provides methods in which a composition comprising a peptide compound described herein is administered to an individual to treat or prevent a disease or condition that is characterized by the generation of toxic levels of ROS or free radicals, including but not limited to tissue and/or cognitive degeneration during aging (senescence), senility, Tardive dyskinesia, cerebral ischemia (stroke), myocardial infarct (heart attack), head trauma, brain and/or spinal cord trauma, reperfusion damage, oxygen toxicity in premature infants, Huntington's disease, Parkinson's disease, amyotrophic lateral sclerosis, Alzheimer's disease, diabetes, ulcerative colitis, human leukemia and other cancers characterized by elevation of ROS or free radicals, age-related elevation of ROS or free radicals, Down syndrome, macular degeneration, cataracts, schizophrenia, epilepsy, septic shock, polytraumatous shock, burn injuries and radiation-induced elevation of ROS and free radicals (including UV-induced skin damage).

In a particularly preferred embodiment, this invention provides methods in which a composition comprising a peptide compound described herein is administered to an individual to lessen or eliminate side effects caused by drug regimens that generate ROS and free radicals. A number of drugs have been found to cause undesirable elevation of levels of ROS or free radicals as a toxic side effect. Such drugs include doxorubicin, daunorubicn, BCNU (carmustine) and related compounds such as methyl-BCNU and CCNU, and neuroleptics, such as clozapine. As an adjuvant to such therapies, the peptide compounds of this invention can be used to decrease the severity of or eliminate these damaging side effects. Accordingly, the peptides of this invention may be administered to treat or prevent drug-induced elevation of ROS or free radicals, such as occurs during treatment with neuroleptic drugs as in Tardive dyskinesia.

In yet another embodiment, the peptide compounds described herein are used as an alternative or adjuvant to nonsteroidal, anti-inflammatory drugs (NSAIDs) to treat pain from wounds, arthritis, and other inflammatory conditions in which ROS and free radicals play a role.

The invention also provides a method of therapeutically or prophylactically treating a disease or disorder, other than stroke, in a mammal in which there is an abnormally high level of ROS or free radicals comprising contacting cells of the mammal with a peptide compound having the formula:

(SEQ ID NO: 16)
$R_1$ Asp Gly Asp Gly Asp Phe Ala Ile Asp Ala
Pro Glu $R_2$, where $R_1$ is absent or is an amino terminal capping group and $R_2$ is absent or is a carboxy terminal capping group of the peptide compound. Preferably, the method uses the peptide compound where the amino terminal capping group $R_1$ is selected from the group consisting of a lipoic acid moiety (in an oxidized or reduced form); a glucose-3-O-glycolic acid group; the acyl group, i.e., $R_3$—CO—, where CO represents a carbonyl group and $R_3$ is a saturated or an unsaturated (mono- or polyunsaturated) hydrocarbon chain having from 1 to 25 (and more preferably 1-22) carbon atoms; 1 to 6 lysine residues; 1 to 6 arginine residues; and combinations thereof. More preferably, the method uses the peptide compound where the amino terminal capping group $R_1$ is an acetyl group, a glucose-3-O-glycolic acid group, or a fatty acid. Even more preferably, $R_1$ is acetyl (Ac), palmitic acid (Palm), lipoic acid (Lip), or docosahexaenoic acid (DHA). In another preferred embodiment, the method uses the peptide compound having the carboxy terminal capping group $R_2$, and, more preferably, wherein $R_2$ is a primary or secondary amine.

The invention also provides therapeutic compositions comprising a peptide compound of the invention in a pharmaceutically acceptable buffer for administration to an individual to eliminate, reduce, or prevent the generation of toxic levels of ROS or free radicals in cells or tissues.

Another aspect of the invention provides dietary supplement compositions (also referred to as "nutraceuticals") comprising a natural source, purified composition obtained from an organism (animal, plant, or microorganism), which contains or is enriched for an endogenous peptide compound described herein, which upregulates expression of one or more genes encoding an antioxidative enzyme, such as SOD and/or CAT in cells or tissues. Preferably, dietary supplements of the invention additionally comprise an exogenously provided peptide compound described herein. In a more preferred embodiment, a natural source of a purified composition from an organism used in making dietary supplement compositions of the invention is green velvet antler from a ruminant, such as deer or elk, or various plant material, such as roots, stems, leaves, flowers, foliage, herbal mixtures, and tea plants.

Certain peptide compounds of the invention may also stimulate or upregulate expression of the gene encoding transcription factor, activator protein 1 (AP-1). AP-1 in turn serves to activate transcription of various AP-1-dependent genes. Accordingly, the invention provides a method of activating transcription factor AP-1 and its transmigration to the cell nucleus and/or stimulating or upregulating the expression of the gene encoding AP-1 transcription factor using a peptide compound described herein, other than a peptide compound having the formula:

$R_1$ Asp Gly Asp Gly Asp Phe Ala Ile Asp Ala Pro Glu $R_2$ (SEQ ID NO: 16), wherein $R_1$ is absent or is any amino terminal capping group as described herein and $R_2$ is absent or is any carboxy terminal capping group as the peptide compound.

BRIEF DESCRIPTION OF THE FIGURES

FIG. 1A shows the gel electrophoresis of RT-PCR product (transcripts) as a function of incubation time (Hours). Each lane was loaded with identical amounts of each cDNA produced by the RT-PCR method for each time point. This was verified by the use of glyceraldehyde-3-phosphate dehydrogenase gene transcript (GAPDH, 451 base pairs), which is a transcript of a housekeeping internal reference gene. The right-hand lane labeled "Pos" is a positive control of upregulation in which cortical cell cultures were stimulated with 10 μg/ml of the peptide compound for 3 hours, showing a maximum development of SOD-1 transcript levels (208 bp). The lane labeled M shows the DNA duplex ladder marker for molecular size. FIG. 1B shows a bar graph depicting quantitative analysis of the data of the upregulation of SOD mRNA. Diagonal line bars indicate SOD-1 data; open bars indicate GAPDH internal reference data.

FIG. 2A shows the dose-response data for the effect of CMX-9236 on the pattern of mRNA synthesis in primary myocyte cultures after a 3-hour incubation with 0, 1, 10, or 100 ng/ml of peptide compound. The analysis used the RT-PCR method as in FIGS. 1A and 1B. The presence of a band at the region of the gel corresponding to 208 base pairs (bp) indicates that SOD-1 was upregulated. FIG. 2B shows a bar graph depicting quantitative analysis of the data, which indicates that the 10 ng/ml and 100 ng/ml doses produced an upregulation of about 6-fold for SOD-1mRNA transcripts. GAPDH is an internal housekeeping reference transcript (as in FIGS. 1A and 1B). Diagonal line bars indicate SOD-1 data; open bars indicate GAPDH internal reference data.

FIG. 3A shows a Western blot containing a band migrating at 34 kDa (the molecular weight of SOD-1), and two lower molecular weight bands corresponding to smaller components recognized by the anti-SOD-1 antibody. FIG. 3B shows a bar graph of the fold-increase in SOD-1 protein as a function of dose of CMX-9967 peptide.

FIG. 4A shows the results of using the RT-PCR method as described in FIG. 1 and specific probes for catalase transcripts. GAPDH is an internal housekeeping standard (451 bp). FIG. 4B shows a bar graph of the fold-increase in catalase and GAPDH (internal standard) transcripts (RT-PCR product) as a function of hours of treatment of the cells with CMX-9236. Diagonal line bars indicate catalase data; open bars indicate GAPDH internal reference data.

FIG. 5A shows the results of the RT-PCR method to detect SOD and catalase mRNA transcripts in rat primary cortical cell cultures incubated for 3 hours with 0, 1, 10, and 100 ng/ml of CMX-9963 or CMX-9967. Enhanced staining at the positions of the 208 and 95 bp regions of the gel corresponding to the correct lengths for the SOD-1 and catalase markers, respectively, were obtained. FIG. 5B shows a bar graph of the quantitative analysis of the data indicating fold-increase as a function of dose of CMX-9963 or CMX-9967. Horizontal line bars indicate SOD-1 data; diagonal line bars indicate catalase data; and open bars indicate GAPDH internal reference data.

FIG. 6A shows the dose-response results for AP-1 activation using the electrophoretic mobility shift assay (EMSA) procedure (see text). The positions of migration corresponding to c-Jun/c-Fos AP-1 heterodimer and to c-Jun/c-Jun AP-1 homodimer are indicated. FIG. 6B shows a quantitative analysis of the data plotted as fold-increase as a function of dose of CMX-9236 peptide. FIG. 6C shows results of EMSAs in which the specificity of the interaction of the probe for AP-1 is illustrated in probe competition experiments in which non-radiolabeled (cold) AP-1 probe and cold mutant AP-1 probe were added to nuclear extracts prior to $P^{32}$ probe addition and prior to electrophoresis. Cold probes were used at OX, 5×, 25×, 50× molar excess relative to the 0.5 pmol of radiolabeled probe. The positions of migration corresponding to c-Jun/c-Fos AP-1 heterodimer and to c-Jun/c-Jun AP-1 homodimer are indicated.

DETAILED DESCRIPTION

Figure 1A:
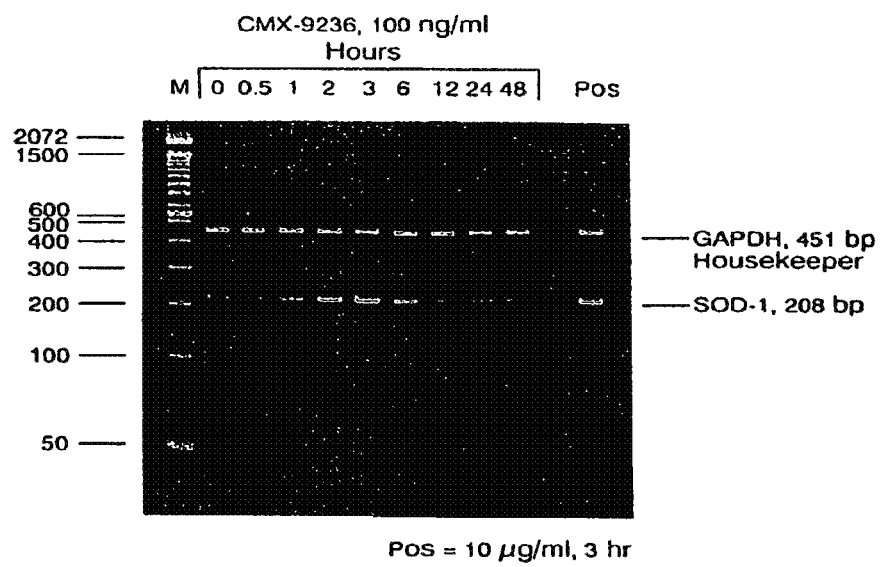
FIGS. 1A and 1B show upregulation of superoxide dismutase-1 (SOD-1) mRNA transcripts of the SOD-1 gene in rat primary cortical cells in cultures incubated for varying amounts of time (0-48 hours) with the peptide compound CMX-9236 (100 ng/ml) as measured by the RT-PCR method (see text).

This invention is based on the discovery of peptide compounds that increase the expression of one or both genes encoding a complementary pair of enzymes, i.e., superoxide dismutase (SOD) and catalase (CAT), which are major components of the antioxidative defense mechanism or system in cells and tissues to detoxify reactive oxygen species (ROS) and free radicals. ROS and free radicals are generated during electron transport and normal respiration and other metabolic processes, including during the metabolism of various drugs, and must be rapidly detoxified to prevent permanent and continuing damage to cells and tissues. In addition, a number of diseases or conditions, including the aging process (senescence), have also been characterized by an elevation of ROS and/or free radicals to toxic levels that in fact damage cells and tissues. Accordingly, the peptide compounds described herein are valuable therapeutic and prophylactic compounds for counteracting the generation of harmful levels of ROS and free radicals in an individual.

In order that the invention may be better understood, the following terms are defined.

Abbreviations: Amino acid residues described herein may be abbreviated by the conventional three letter or one letter abbreviation know in the art (see, e.g., Lehninger, A. L., *Biochemistry*, second edition (Worth Publishers, Inc., New York, 1975), p. 72). Other abbreviations used herein include: "DHA" for a docosahexaenoic acid moiety; "Lip" for a lipoic acid moiety; "Palm" for a palmitic acid moiety (i.e., a palmitoyl group); "Ac" for an acetyl moiety; "Gga" for a glucose-3-O-glycolic acid moiety; "SOD" for super oxide dismutase; "CAT" for catalase; "GAPDH" for glyceraldehyde-3-phosphate dehydrogenase; and "ROS" for reactive oxygen species. Still other abbreviations are indicated as needed elsewhere in the text.

"Hydrocarbon" refers to either branched or unbranched and saturated or unsaturated hydrocarbon chains. Preferred hydrocarbon chains found in some of the peptide compounds described herein contain between 1 and 25. More preferred are hydrocarbon chains between 1 and 22 carbon atoms.

"Reactive oxygen species" or "ROS", as understood and used herein, refers to highly reactive and toxic oxygen compounds that are generated in the course of normal electron transport system during respiration or that are generated in a disease or during treatment with certain therapeutic agents for a particular disorder. ROS include, but are not limited to, the superoxide anion ($O_2.^-$), hydrogen peroxide ($H_2O_2$), singlet oxygen, lipid peroxides, and peroxynitrite.

"Free radical", as understood and used herein, refers to any atom or any molecule or compound that possesses an odd (unpaired) electron. By this definition, the superoxide anion is also considered a negatively charged free radical. The free radicals of particular interest to this invention are highly reactive, highly oxidative molecules that are formed or generated during normal metabolism, in a diseased state, or during treatment with chemotherapeutic drugs. Such free radicals are highly reactive and capable of causing oxidative damage to molecules, cells and tissues. One of the most common and potentially destructive types of the free radicals other than the superoxide anion is a hydroxyl radical. Typically, the generation of ROS, such as superoxide anion or singlet oxygen, also leads to one or more other harmful free radicals as well. Accordingly, phrases such as "ROS and free radicals" or "ROS and other free radicals", as understood and used herein, are meant to encompass any or all of the entire population of highly reactive, oxidative molecular species or compounds that may be generated in a particular metabolic state or condition of cells and tissues of interest (see, for example, Somani et al, "Response of Antioxidant System To Physical and Chemical Stress," In *Oxidants. Antioxidants, and Free Radicals*, chapter 6: 125-141 (Taylor & Francis, Washington, D.C., 1997)).

"Oxygen radical scavengers" or "lazaroids" are a class of compounds that have an ability to scavenge and detoxify ROS and free radicals. Vitamins A, C, E, and related antioxidant compounds, such as β-carotene and retinoids, are also members of this large class of compounds, as are antioxidative enzymes, such as SOD and CAT. In healthy individuals, sufficient levels of antioxidative enzymes and other lazaroids are present both intracellularly and extracellularly to efficiently scavenge sufficient amounts of ROS and free radicals to avoid significant oxidative damage to cells and tissues.

"Peptide compound", as understood and used herein, refers to any compound that contains at least one peptide bond. "Peptide compound" includes unmodified or underivatized peptides, typically containing fewer than about 20 amino acids, as well as derivatives of peptides. Derivative or derivatized peptides contain one or more chemical moieties other than amino acids that are covalently attached at the amino terminal amino acid residue, the carboxy terminal amino acid residue, or at an internal amino acid residue.

"Natural source purified", as understood and used herein, describes a composition of matter purified or extracted from an organism or collection of organisms occurring in nature or in a cultivated state that have not been altered genetically by in vitro recombinant nucleic acid technology, including but not limited to animals, any species of crops used for beverage and food, species of uncultivated plants growing in nature, species of plants developed from plant breeding, and microorganisms that have not been altered genetically by in vitro recombinant technology. Particularly preferred natural sources for preparing natural source purified compositions of matter of the invention are green velvet antler of ruminants, such as deer and cattle, and plant tissue, such as roots, stems, leaves, and flowers from plants used as herbs and teas.

An "amino terminal capping group" of a peptide compound described herein is any chemical compound or moiety that is covalently linked or conjugated to the amino terminal amino acid residue of a peptide compound. The primary purpose of such an amino terminal capping group is to inhibit or prevent intramolecular cyclization or intermolecular polymerization, to promote transport of the peptide compound across the blood-brain barrier, or to provide a combination of these properties. A peptide compound of this invention that possesses an amino terminal capping group may possess other beneficial activities as compared with the uncapped peptide, such as enhanced efficacy or reduced side effects. For example, several of the amino terminal capping groups used in the peptide compounds described herein also possess antioxidative activity in their free state (e.g., lipoic acid) and thus, may improve or enhance the antioxidative activity of the peptide in its uncapped form. Examples of amino terminal capping groups that are useful in preparing peptide compounds and compositions according to this invention include, but are not limited to, 1 to 6 lysine residues, 1 to 6 arginine residues, a mixture of arginine and lysine residues ranging from 2 to 6 residues, urethanes, urea compounds, a lipoic acid ("Lip") or a palmitic acid moiety (i.e., palmitoyl group, "Palm"), glucose-3-O-glycolic acid moiety ("Gga"), or an acyl group that is covalently linked to the amino terminal amino acid residue of the peptide. Such acyl groups useful in the compositions of the invention may have a carbonyl group and a hydrocarbon chain that ranges from one carbon atom (e.g., as in an acetyl moiety) to up to 25 carbons (such as docosahexaenoic acid, "DHA", which has a hydrocarbon chain that contains 22 carbons). Furthermore, the carbon chain of the acyl group may be saturated, as in a palmitic acid, or unsaturated. It should be understood that when an acid (such as DHA, Palm, or Lip) is present as an amino terminal capping group, the resultant peptide compound is the condensed product of the uncapped peptide and the acid.

A "carboxy terminal capping group" of a peptide compound described herein is any chemical compound or moiety that is covalently linked or conjugated to the carboxy terminal amino acid residue of the peptide compound. The primary purpose of such a carboxy terminal capping group is to inhibit or prevent intramolecular cyclization or intermolecular polymerization, to promote transport of the peptide compound across the blood-brain barrier, or to provide a combination of these properties. A peptide compound of this invention possessing a carboxy terminal capping group may possess other beneficial activities as compared with the uncapped peptide, such as enhanced efficacy, reduced side effects, enhanced hydrophilicity, enhanced hydrophobicity, or enhanced antioxidative activity, e.g., if the carboxy terminal capping moiety possesses a source of reducing potential, such as one or more sulfhydryl groups. Carboxy terminal capping groups that are particularly useful in the peptide compounds described herein include primary or secondary amines that are linked by an amide bond to the α-carboxyl group of the carboxy terminal amino acid of the peptide compound. Other carboxy terminal capping groups useful in the invention include aliphatic primary and secondary alcohols and aromatic phenolic derivatives, including flavenoids, with C1 to C26 carbon atoms, which form esters when linked to the carboxylic acid group of the carboxy terminal amino acid residue of a peptide compound described herein.

Peptide compounds of the invention also include any peptide containing modifications of the side chain of one or more amino acid residues within the peptide chain. Such modifications include (without limitation) conservative amino acid substitutions, addition of protective or capping groups on reactive moieties, and other changes that do not adversely destroy the activity of the peptide (i.e., its antioxidative activity and/or its ability to stimulate expression of a gene encoding SOD and/or CAD.

"Radiation", as understood and used herein, means any type of propagating or emitted energy wave or energized particle, including electromagnetic radiation, ultraviolet radiation (UV), and other sunlight-induced radiation and radioactive radiation. The effects of such radiation may affect the surface or underlayers of the skin or may produce systemic damage at a remote site in the body.

"Upregulate" and "upregulation", as understood and used herein, refer to an elevation in the level of expression of a gene product in a cell or tissue. The peptide compounds described herein are capable of upregulating expression of genes encoding superoxide dismutase (SOD), catalase (CAT), and/or AP-1 transcription factor (AP-1) beyond the levels normally found in cells and tissues that have not been treated (contacted) with the peptide compounds. Thus, an elevation in the level of SOD, CAT, or AP-1 mRNA transcript; in SOD, CAT, or AP-1 gene product (protein) synthesis; in the level of SOD or CAT enzyme activity, or in the level of an AP-1 factor dependent transcription activity indicate upregulation of gene expression. Expression of SOD, CAT, and AP-1 genes can be detected by a variety of ways, including Northern blotting to detect mRNA transcripts encoding the enzyme, by Western immunoblotting to detect the gene product, in the case of SOD and CAT, by using standard assays for SOD or CAT enzymatic activities, or in the case of AP-1, by using an AP-1 dependent transcription expression assay.

"Nutraceutical" and "dietary supplement", as understood and used herein, are synonymous terms, which describe compositions that are prepared and marketed for sale as non-regulated, orally administered, sources of a nutrient and/or other compound that is purported to contain a property or activity that may provide a benefit to the health of an individual. A desirable component compound identified in a dietary supplement is referred to as a "nutrichemical". Nutrichemicals may be present in only trace amounts and still be a desirable and marketable component of a dietary supplement. Commonly known nutrichemicals include trace metals, vitamins, enzymes that have an activity that is considered beneficial to the health of an individual, and compounds that upregulate such enzymes. Such enzymes include antioxidative enzymes, such as superoxide dismutase (SOD) and catalase (CAT), which counteract the harmful oxidative effects of reactive oxygen species (ROS) and other free radicals. Accordingly, one or more peptide compounds described herein that is endogenously present and/or added exogenously to a composition manufactured for sale as a dietary supplement is a nutrichemical of that dietary supplement.

Other terms will be evident as used in the following description.

Peptide Compounds and Compositions

The invention provides peptide compounds described herein for use in compositions and/or methods that are not previously described in the art and that are capable of upregulating SOD and/or CAT in eukaryotic cells, which have at least one functional gene encoding the SOD and/or CAT enzymes. Upregulating levels of SOD and/or CAT in cells or tissues provides an enhanced detoxification system to prevent, reduce, or eliminate the harmful oxidative activity of ROS and free radicals. Preferred peptides and peptide compounds of this invention upregulate both SOD and CAT. The peptide compounds described herein may also upregulate the AP-1 transcription factor, which inter alia may enhance expression of antioxidative gene products and/or growth factors.

The peptide compounds provided by the invention are preferably less than about 20, and, in order of increasing preference, less than about 18, 15, 13, 9, 6, 5, 4 and 3, amino acids in length and are able to upregulate expression of a gene(s) for SOD and/or CAT in cells and tissues. Such activity may be tested in vitro, e.g., in tissue culture. The peptide compounds of the invention show upregulation activity at low concentrations, i.e., in the range of nanograms of peptide compound per milliliter (ml). Such high potency is similar to that exhibited by various hormones, such as luteinizing hormone releasing hormone (LHRH) or human growth hormone. Accordingly, the peptide compounds described herein may be prepared, stored, and used employing much of the available technology already applied to the preparation, storage, and administration of known therapeutic hormone peptides.

The peptide compounds described herein may contain a peptide to which additional modifications have been made, such as addition of chemical moieties at the amino terminal and/or carboxy terminal amino acid residues of the peptide, conservative amino acid substitutions or modifications of side chains of internal amino acid residues of the peptide that do not destroy the desired activity of the peptide. It has been observed that intramolecular cyclization and some intermolecular polymerizations of the peptide compounds described herein tend to inactivate or decrease the activity of the peptide compound so that the peptide compound cannot effectively upregulate SOD, CAT, or AP-1. Accordingly, the most useful peptide compounds are the least susceptible to cyclization reactions and polymerization or conjugation with other peptide compound molecules. In addition to maintaining or enhancing the ability of these peptides to upregulate SOD, CAT and/or AP-1, such modifications may advantageously confer additional benefits. For example, amino terminal capping groups may promote transport of the peptide compound across the blood-brain barrier (see, for example, PCT publication WO 99/26620). This property is particularly important when a peptide compound is used to upregulate SOD and CAT in brain tissue and parts of the central nervous system. Amino terminal capping groups that promote transport across the blood-brain barrier may also prevent cyclization of the peptide compound to which they are attached or may prevent polymerization with other peptide compounds.

Preferred amino terminal capping groups include a lipoic acid moiety, which can be attached by an amide linkage to the α-amino group of the amino terminal amino acid of a peptide.

Lipoic acid ("Lip") in its free form possesses independent antioxidative activity and may enhance the antioxidative activity of the peptides of this invention when used as an amino terminal capping group. An amino terminally linked lipoic acid moiety may be in its reduced form where it contains two sulfhydryl groups or in its oxidized form in which the sulfhydryl groups are oxidized and form an intramolecular disulfide bond and, thereby, a heterocyclic ring structure. Another amino terminal capping group useful in preparing peptide compounds of the invention is a glucose-3-O-glycolic acid moiety ("Gga"), which can be attached in an amide linkage to the α-amino group of the amino terminal amino acid of a peptide compound. The glucose moiety may also contain further modifications, such as an alkoxy group replacing one or more of the hydroxyl groups on the glucose moiety.

Another example of an amino terminal capping group useful in the peptide compounds described herein is an acyl group, which can be attached in an amide linkage to the α-amino group of the amino terminal amino acid residue of a peptide compound. The acyl group has a carbonyl group linked to a saturated or unsaturated (mono- or polyunsaturated), branched or unbranched, hydrocarbon chain of 1 to 25 carbon atoms in length, and more preferably, the hydrocarbon chain of the acyl group is 1 to 22 carbon atoms in length, as in DHA. The acyl group preferably is acetyl or a fatty acid. The fatty acid used as the acyl amino terminal capping group may contain a hydrocarbon chain that is saturated or unsaturated and that is either branched or unbranched. Preferably the hydrocarbon chain is 1 to 25 carbon atoms in length, and more preferably the length of the hydrocarbon chain is 1-22 carbon atoms in length. For example, fatty acids that are useful as amino terminal capping groups for the peptide compounds of this invention include, but are not limited to: caprylic acid (C8:0), capric acid (C10:0), lauric acid (C12:0), myristic acid (C14:0), palmitic acid ("Palm") (C16:0), palmitoleic acid (C16:1), C16:2, stearic acid (C18:0), oleic acid (C18:1), vaccenic acid (C18:1-7), linoleic acid (C18:2-6), α-linolenic acid (C18:3-3), eleostearic acid (C18:3-5), β-linolenic acid (C18:3-6), C18:4-3, gondoic acid (C20:1), C20:2-6, dihomo-γ-linolenic acid (C20:3-6), C20:4-3, arachidonic acid (C20: 4-6), eicosapentaenoic acid (C20:5-3), docosenoic acid (C22: 1), docosatetraenoic acid (C22:4-6), docosapentaenoic acid (C22:5-6), docosapentaenoic acid (C22:5-3), docosahexaenoic acid ("DHA") (C22:6-3), and nervonic acid (C24: 1-9). Particularly preferred fatty acids used as acyl amino terminal capping groups for the peptide compounds described herein are palmitic acid (Palm) and docosahexaenoic acid (DHA). DHA and various other fatty acid moieties appear to promote transport of molecules to which they are linked across the blood-barrier (see, for example, PCT publication WO 99/40112 and PCT publication WO 99/26620). Accordingly, such fatty acyl moieties are particularly preferred when a peptide compound described herein will be administered to counteract the oxidative effects of ROS and free radicals in brain tissue and/or other parts of the central nervous system.

In addition, in certain cases the amino terminal capping group may be a lysine residue or a polylysine peptide, preferably where the polylysine peptide consists of two, three, four, five or six lysine residues, which can prevent cyclization, crosslinking, or polymerization of the peptide compound. Longer polylysine peptides may also be used. Another amino terminal capping group that may be used in the peptide compounds described herein is an arginine residue or a polyarginine peptide, preferably where the polyarginine peptide consists of two, three, four, five, or six arginine residues, although longer polyarginine peptides may also be used. An amino terminal capping group of the peptide compounds described herein may also be a peptide containing both lysine and arginine, preferably where the lysine and arginine containing peptide is two, three, four, five or six residue combinations of the two amino acids in any order, although longer peptides that contain lysine and arginine may also be used. Lysine and arginine containing peptides used as amino terminal capping groups in the peptide compounds described herein may be conveniently incorporated into whatever process is used to synthesize the peptide compounds to yield the derivatized peptide compound containing the amino terminal capping group.

The peptide compounds useful in the compositions and methods of the invention may contain a carboxy terminal capping group. The primary purpose of this group is to prevent intramolecular cyclization or inactivating intermolecular crosslinking or polymerization. However, as noted above, a carboxy terminal capping group may provide additional benefits to the peptide compound, such as enhanced efficacy, reduced side effects, enhanced antioxidative activity, and/or other desirable biochemical properties. An example of such a useful carboxy terminal capping group is a primary or secondary amine in an amide linkage to the carboxy terminal amino acid residue. Such amines may be added to the α-carboxyl group of the carboxy terminal amino acid of the peptide using standard amidation chemistry.

The peptide compounds used in the compositions and methods of the invention may contain amino acids with charged side chains, i.e., acidic and basic amino acids. Most preferably, if a peptide compound contains charged amino acids, then the charged amino acids are either all acidic amino acids, i.e., negatively charged, or are all basic amino acids, i.e., positively charged. Such uniformity in charged amino acids contributes to stability of the peptide compounds and prevents the formation of cyclic, crosslinked or polymerized forms of a peptide compound during storage or during use in vivo. Cyclization, crosslinking, or polymerization of a peptide compound described herein may abolish all or so much of the activity of the peptide compound so that it cannot be used in the therapeutic or prophylactic compositions and methods of the invention. Furthermore, some cyclic peptide compounds are potentially toxic. Accordingly, if a peptide compound contains basic (positively charged) amino acid residues, then it is recommended that the carboxy terminal carboxylic acid group be converted to an amide (i.e., by use of a carboxy terminal capping group) to prevent the carboxylic acid group from reacting with a free amino group in the same peptide compound to form a cyclic compound or in a different peptide compound to form a polymerized or crosslinked peptide compound.

In addition, peptide compounds described herein may contain one or more D-amino acid residues in place of one or more L-amino acid residues provided that the incorporation of the one or more D-amino acids does not abolish all or so much of the activity of the peptide compound that it cannot be used in the compositions and methods of the invention. Incorporating D-amino acids in place of L-amino acids may advantageously provide additional stability to a peptide compound, especially in vivo.

The peptide compounds can be made using standard methods or obtained from a commercial source. Direct synthesis of the peptides of the peptide compounds of the invention may be accomplished using conventional techniques, including solid-phase peptide synthesis, solution-phase synthesis, etc. Peptides may also be synthesized using various recombinant nucleic acid technologies, however, given their relatively small size and the state of direct peptide synthesis technology, a direct synthesis is preferred and solid-phase synthesis is most preferred. In solid-phase synthesis, for example, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents, and reaction conditions used throughout the synthesis and are removable under conditions, which do not affect the final peptide product. Stepwise synthesis of the polypeptide is carried out by the removal of the N-protecting group from the initial (i.e., carboxy terminal) amino acid, and coupling thereto of the carboxyl end of the next amino acid in the sequence of the polypeptide. This amino acid is also suitably protected. The carboxyl group of the incoming amino acid can be activated to react with the N-terminus of the bound amino acid by formation into a reactive group such as formation into a carbodiimide, a symmetric acid anhydride, or an "active ester" group such as hydroxybenzotriazole or pentafluorophenyl esters. The preferred solid-phase peptide synthesis methods include the BOC method, which utilizes tert-butyloxycarbonyl as the α-amino protecting group, and the FMOC method, which utilizes 9-fluorenylmethloxycarbonyl to protect the α-amino of the amino acid residues, both methods of which are well-known by those of skill in the art (see, Stewart et al., *Solid-Phase Peptide Synthesis* (W. H. Freeman Co., San Francisco 1989); Merrifield, *J. Am. Chem. Soc.*, 85:2149-2154 (1963); Bodanszky and Bodanszky, *The Practice of Peptide Synthesis* (Springer-Verlag, New York 1984), incorporated herein by reference).

Peptide compounds according to the invention may also be prepared commercially by companies providing peptide synthesis as a service (e.g., BACHEM Bioscience, Inc., King of Prussia, Pa.; AnaSpec, Inc., San Jose, Calif.). Automated peptide synthesis machines, such as manufactured by Perkin-Elmer Applied Biosystems, also are available.

Peptide compounds useful in the compositions and methods of the invention may also be prepared and used in a salt form. Typically, a salt form of a peptide compound will exist by adjusting the pH of a composition comprising the peptide compound with an acid or base in the presence of one or more ions that serve as counter ion to the net ionic charge of the peptide compound at the particular pH. Various salt forms of the peptide compounds described herein may also be formed or interchanged by any of the various methods known in the art, e.g., by using various ion exchange chromatography methods. Cationic counter ions that may be used in the compositions described herein include, but are not limited to, amines, such as ammonium ion; metal ions, especially monovalent, divalent, or trivalent ions of alkali metals (e.g., sodium, potassium, lithium, cesium), alkaline earth metals (e.g., calcium, magnesium, barium), transition metals (e.g., iron, manganese, zinc, cadmium, molybdenum), other metals (e.g., aluminum); and combinations thereof. Anionic counter ions that may be used in the compositions described herein include, but are not limited to, chloride, fluoride, acetate, trifluoroacetate, phosphate, sulfate, carbonate, citrate, ascorbate, sorbate, glutarate, ketoglutarate, and combinations thereof. Trifluoroacetate salts of peptide compounds described herein are typically formed during purification in trifluoroacetic acid buffers using high-performance liquid chromatography (HPLC). While generally not suited for in vivo use, trifluoroacetate salt forms of the peptide compounds described herein may be conveniently used in various in vitro cell culture studies or assays performed to test the activity or efficacy of a peptide compound of interest. The peptide compound may then be converted from the trifluoroacetate salt (e.g., by ion exchange methods) to or synthesized as a salt form that is acceptable for pharmaceutical or dietary supplement (nutraceutical) compositions.

A peptide compound useful in the methods of the invention is preferably purified once it has been isolated or synthesized by either chemical or recombinant techniques. For purification purposes, there are many standard methods that may be employed including reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptide compounds based on their charge. The degree of purity of the peptide compound may be determined by various methods, including identification of a major large peak on HPLC. A peptide compound that produces a single peak that is at least 95% of the input material on an HPLC column is preferred. Even more preferable is a polypeptide that produces a single peak that is at least 97%, at least 98%, at least 99% or even 99.5% of the input material on an HPLC column.

In order to ensure that a peptide compound obtained using any of the techniques described above is the desired peptide compound for use in compositions and methods of the present invention, analysis of the compound's composition determined by any of a variety of analytical methods known in the art. Such composition analysis may be conducted using high resolution mass spectrometry to determine the molecular weight of the peptide. Alternatively, the amino acid content of a peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide. Since some of the peptide compounds contain amino and/or carboxy terminal capping groups, it may be necessary to remove the capping group or the capped amino acid residue prior to a sequence analysis. Thin-layer chromatographic methods may also be used to authenticate one or more constituent groups or residues of a desired peptide compound.

The various peptide compounds described herein are useful in the compositions and methods of the invention to upregulate the expression of a gene encoding SOD and/or CAT and thereby generate antioxidative activity to counteract the undesirable and destructive oxidative activity of ROS and free radicals, e.g., as generated in the aging process (senescence), disease, and various drug treatments. Preferred peptide compounds, excluding any amino and/or carboxy terminal capping group (i.e., the "core sequence"), are less than 20 amino acids in length. In particular, such preferred peptide compounds, in the absence of amino and carboxy terminal capping groups, are less than 18, 15, 13, 9, 6, 5, 4, and even 3 amino acids in length. A peptide useful in the compositions and methods of the invention may be 3 or even 2 amino acids in length (core sequence), such as the preferred dipeptide compound that has an amino acid sequence consisting of Asp Gly. Any amino terminal and/or carboxy terminal capping group described herein may be added to such preferred peptide compounds, provided the capping group does not also react with other groups in the peptide to result in a significant or toxic amount of undesirable cyclization or polymerization.

The invention provides a peptide compound having the formula:

R₁ Gln Tyr Lys Leu Gly Ser Lys Thr Gly Pro Gly Gln R₂,    (SEQ ID NO: 1)

wherein R₁ is absent or is an amino terminal capping group; R₂ is absent or is a carboxy terminal capping group of the peptide compound; and wherein the peptide compound upregulates expression of a gene encoding an antioxidative enzyme.

In another embodiment, the invention provides a peptide compound having the formula:

R₁ Gln Thr Leu Gln Phe Arg R₂,    (SEQ ID NO: 2)

wherein R₁ is absent or is an amino terminal capping group; R₂ is absent or is a carboxy terminal capping group of the peptide compound; and wherein the peptide compound upregulates expression of a gene encoding an antioxidative enzyme.

In yet another embodiment, the invention provides a peptide compound having the formula:

R₁ Xaa₁ Gly Xaa₂ Xaa₃ Xaa₄ Xaa₅ Xaa₆ R2,    (SEQ ID NO: 3)

wherein Xaa₁ and Xaa₂ are, independently, aspartic acid or asparagine; R₁ is absent or is an amino terminal capping group of the peptide compound; Xaa₃ is absent or Gly; Xaa₄ is absent, Asp, or Phe; Xaa₅ is absent, Ala, or Phe; Xaa₆ is absent or Ala; R₂ is absent or is a carboxy terminal capping group of the peptide compound; and wherein the peptide compound upregulates expression of a gene encoding an antioxidative enzyme. A preferred peptide compound according to the formula, upregulates expression of a gene encoding an antioxidative enzyme and comprises an amino acid sequence selected from the group consisting of:

```
Asp Gly Asp

Asp Gly Asn

Asn Gly Asn

Asn Gly Asp

Asp Gly Asp Gly Asp,         (SEQ ID NO: 4)

Asp Gly Asp Gly Phe Ala,     (SEQ ID NO: 5)

Asp Gly Asp Gly Asp Phe Ala, (SEQ ID NO: 6)

Asp Gly Asn Gly Asp Phe Ala, (SEQ ID NO: 7)

Asn Gly Asn Gly Asp Phe Ala, (SEQ ID NO: 8)
and

Asn Gly Asp Gly Asp Phe Ala. (SEQ ID NO: 9)
```

The invention also provides a peptide compound having the formula:

R₁ Asn Ser Thr R₂, wherein R₁ is absent or is an amino terminal capping group; R₂ is absent or is a carboxy terminal capping group of the peptide compound; and wherein the peptide compound upregulates expression of a gene encoding an antioxidative enzyme.

In still another embodiment, the invention provides a peptide compound having the formula:

R₁ Phe Asp Gln R₂, wherein R₁ is absent or is an amino terminal capping group; R₂ is absent or is a carboxy terminal capping group of the peptide compound; and wherein the peptide compound upregulates expression of a gene encoding an antioxidative enzyme.

The invention also provides a peptide compound having the formula:

R₁ Xaa₁ Xaa₂ Met Thr Leu Thr Gln Pro R₂,    (SEQ ID NO: 10)

wherein Xaa₁ is absent or Ser; Xaa₂ is absent or Lys; R₁ is absent or an amino terminal capping group; R₂ is absent or a carboxy terminal capping group of the peptide compound; and wherein the peptide compound upregulates expression of a gene encoding an antioxidative enzyme. A preferred peptide compound according to the formula upregulates expression of a gene encoding an antioxidative enzyme and comprises an amino acid sequence selected from the group consisting of Met Thr Leu Thr Gln Pro    (SEQ ID NO: 11)
and Ser Lys Met Thr Leu Thr Gln Pro.    (SEQ ID NO: 12)

Another aspect of the invention is a peptide compound having the formula:

Xaa₁ Xaa₂ Xaa₃ R₂, wherein Xaa₁ is Asp, Asn, Glu, Gln, Thr, or Tyr; Xaa₂ is absent or any amino acid (i.e., is variable); Xaa₃ is Asp, Asn, Glu, Thr, Ser, Gly, or Leu; R₁ is absent or is an amino terminal capping group and R₂ is absent or is a carboxy terminal capping group of the peptide compound; wherein the peptide compound upregulates expression of a gene encoding an antioxidative enzyme. Preferably, a peptide compound of the formula upregulates expression of a gene encoding an antioxidative enzyme and comprises the above formula wherein Xaa₂ is selected from the group consisting of Val, Gly, Glu, and Gln. More preferably, the peptide compound of the formula upregulates expression of a gene encoding an antioxidative enzyme and is selected from the group consisting of: Asp Gly, Asn Gly, Glu Gly, Gln Gly, Thr Val Ser, Asp Gly Asp, and Asn Gly Asn.

In still another embodiment, the invention provides a peptide compound having the formula:

R₁ Leu Xaa₁ Xaa₂ R₂, wherein Xaa₁ is any amino acid; Xaa₂ is Gln, Gly, or Tyr; R₁ is absent or is an amino terminal capping group; R₂ is absent or is a carboxy terminal capping group of the peptide; and wherein the peptide compound upregulates expression of a gene encoding an antioxidative enzyme compound.

The invention also provides a peptide compound having the formula:

R₁ Met Thr Xaa₁ R₂, wherein Xaa₁ is Asn, Asp, Glu, Thr, or Leu; R₁ is absent or is an amino terminal capping group; R₂ is absent or is a carboxy terminal capping group of the peptide compound; and wherein the peptide compound upregulates expression of a gene encoding an antioxidative enzyme. Preferably, the peptide compound of the formula upregulates expression of a gene encoding an antioxidative enzyme and comprising an amino acid sequence selected from the group consisting of Met Thr Leu; Met Thr Asp; Met Thr Asn; Met Thr Thr; Met Thr Glu; and Met Thr Gln.

In a preferred embodiment, a peptide compound of any of the formulas described herein has the $R_1$ amino terminal capping group. More preferably, the $R_1$ amino terminal capping group is selected from the group consisting of a lipoic acid moiety (Lip, in reduced or oxidized form); a glucose-3-O-glycolic acid moiety (Gga); 1 to 6 lysine residues; 1 to 6 arginine residues; an acyl group of the formula $R_3$—CO—, where CO is a carbonyl group, and $R_3$ is a hydrocarbon chain having from 1 to 25 carbon atoms, and preferably 1 to 22 carbon atoms, and where the hydrocarbon chain may be saturated or unsaturated and branched or unbranched; and combinations thereof. More preferably, when the amino terminal capping group is an acyl group it is acetyl or a fatty acid. Even more preferably, the amino terminal capping group is an acyl group selected from the group consisting of acetyl (Ac), palmitic acid (i.e., a palmitoyl group, Palm), and docosahexaenoic acid (DHA). In another embodiment, the amino terminal capping group is a peptide consisting of any combination of arginine and lysine wherein the peptide is not less than two amino acids in length and not more than six amino acids in length.

Particularly preferred peptide compounds that upregulate a gene encoding an antioxidative enzyme and that are useful in compositions and methods of the invention include, but are not limited to, peptide compounds comprising an amino acid sequence selected from the group consisting of:

```
                                              (SEQ ID NO: 1)
Gln Tyr Lys Leu Gly Ser Lys Thr Gly Pro Gly Gln, (SEQ ID NO: 2)
Gln Thr Leu Gln Phe Arg, (SEQ ID NO: 13)
Glu Thr Leu Gln Phe Arg, (SEQ ID NO: 14)
Gln Tyr Ser Ile Gly Gly Pro Gln, (SEQ ID NO: 15)
Ser Asp Arg Ser Ala Arg Ser Tyr, (SEQ ID NO: 12)
Ser Lys Met Thr Leu Thr Gln Pro, (SEQ ID NO: 13)
Met Thr Leu Thr Gln Pro, (SEQ ID NO: 16)
Asp Gly Asp Gly Asp Phe Ala Ile Asp Ala Pro Glu, (SEQ ID NO: 6)
Asp Gly Asp Gly Asp Phe Ala, (SEQ ID NO: 4)
Asp Gly Asp Gly Asp, (SEQ ID NO: 8)
Asn Gly Asn Gly Asp Phe Ala, (SEQ ID NO: 17)
Asn Gly Asn Gly Asp, (SEQ ID NO: 7)
Asp Gly Asn Gly Asp Phe Ala, (SEQ ID NO: 18)
Asp Gly Asn Gly Asp, (SEQ ID NO: 9)
Asn Gly Asp Gly Asp Phe Ala, (SEQ ID NO: 19)
Asn Gly Asp Gly Asp, (SEQ ID NO: 20)
Asn Gly Asp Gly, (SEQ ID NO: 5)
Asp Gly Asp Gly Phe Ala, (SEQ ID NO: 21)
Asn Gly Asn Gly Phe Ala, (SEQ ID NO: 22)
Asp Gly Asn Gly Phe Ala, (SEQ ID NO: 23)
Asn Gly Asp Gly Phe Ala,
```

Asp Gly Asp, Asn Gly Asn, Asp Gly Asn, Asn Gly Asp, Asn Ser Thr, Phe Asp Gln, Met Thr Leu, Met Thr Asp, Met Thr Asn, Met Thr Thr, Met Thr Glu, Met Thr Gln, Thr Val Ser, Leu Thr Gln, Leu Thr Gly, Leu Thr Tyr, Asp Gly, Asn Gly, Glu Gly, Gln Gly, Glu Ala, Gln Ala, Gln Gly, Asp Ala, and Asn Ala.

A particularly preferred peptide compound of the invention that upregulates a gene encoding an antioxidative enzyme and that is useful in compositions and methods of the invention comprises an amino acid sequence selected from the group consisting of: Asp Gly Asp, Thr Val Ser, Asp Gly, and Glu Ala.

Such preferred peptide compounds as listed above may also contain one or more terminal capping groups, such as an amino terminal capping group and/or a carboxy terminal capping group described herein. Preferred peptide compounds containing one or more terminal capping groups that upregulate an antioxidative enzyme and that are useful in the compositions and methods include, but are not limited to, peptide compounds having the formulas:

```
                                              (SEQ ID NO: 25)
    Lys Lys Glu Thr Leu Gln Phe Arg;

(SEQ ID NO: 26)
    Lys Lys Gln Thr Leu Gln Phe Arg;

(SEQ ID NO: 27)
    Lys Lys Asp Gly Asp Gly Asp Phe Ala Ile Asp
    Ala Pro Glu;

(SEQ ID NO: 27)
    DHA Lys Lys Asp Gly Asp Gly Asp Phe Ala Ile
    Asp Ala Pro Glu;

(SEQ ID NO: 11)
    Palm Asp Gly Asp Gly Asp Phe Ala Ile Asp Ala
    Pro Glu;

(SEQ ID NO: 12)
    Gga Asp Gly Asp Gly Asp Phe Ala;

(SEQ ID NO: 12)
    Ac Asp Gly Asp Gly Asp Phe Ala;

(SEQ ID NO: 12)
    Palm Asp Gly Asp Gly Asp Phe Ala;

(SEQ ID NO: 13)
    Gga Asp Gly Asp Gly Asp;
```

-continued

```
                                              (SEQ ID NO: 13)
Palm Asp Gly Asp Gly Asp;

(SEQ ID NO: 13)
Lip Asp Gly Asp Gly Asp;

(SEQ ID NO: 13)
DHA Asp Gly Asp Gly Asp;

(SEQ ID NO: 13)
(Lys)$_n$ Asp Gly Asp Gly Asp;
```

Ac-Thr Val Ser; Lip Thr Val Ser; Gga Asp Gly Asp; Palm Asp Gly Asp; Lip Asp Gly Asp; DHA Asp Gly Asp; (Lys)$_n$ Asp Gly Asp; Gga Phe Asp Gln; Palm Phe Asp Gln; Lip Phe Asp Gln; DHA Phe Asp Gln; (Lys)$_n$ Phe Asp Gln; Gga Asn Ser Thr; Palm Asn Ser Thr; Lip Asn Ser Thr; DHA Asn Ser Thr; (Lys). Asn Ser Thr; Gga Asp Gly; Palm Asp Gly; Lip Asp Gly; DHA Asp Gly; (Lys)$_n$ Asp Gly; Gga Asn Gly; Palm Asn Gly; Lip Asn Gly; DHA Asn Gly; (Lys)$_n$ Asn Gly; Gga Glu Ala; Palm Glu Ala; DHA Glu Ala; (Lys)$_n$ Glu Ala; Gga Gln Ala; Palm Gln Ala; DHA Gln Ala; (Lys)$_n$ Gln Ala; Gga Glu Gly; Palm Glu Gly; DHA Glu Gly; (Lys)$_n$ Glu Gly; Gga Glu Gly; Palm Glu Gly; DHA Glu Gly; (Lys)$_n$ Glu Gly; Gga Gln Gly; Palm Gln Gly; DHA Gln Gly; and (Lys)$_n$ Gln Gly, wherein Palm is a palmitic acid (palmitoyl) group, Lip is lipoic acid group, in either oxidized or reduced form; Ac is an acetyl group; DHA is an docosahexaenoic acid group; Gga is a glucose-3-O-glycolic acid group; and n in (Lys)$_n$ is 1-6. These preferred peptide compounds may also contain a carboxy terminal capping group, such as a primary amino group in amide linkage to the carboxy terminal amino acid.

One aspect of the invention contemplates a metabolically convertible form of an peptide compound of the invention wherein asparagine and glutamine residues in the amino acid sequence of the peptide compounds are converted in a cell to their corresponding acid form, or salt thereof in physiological conditions, i.e., aspartic acid (or aspartate) and glutamic acid (or glutamate). For example, peptides consisting of the amino acid sequences Asn Gly and Gln Gly are contemplated to be metabolically converted to the corresponding peptides consisting of Asp Gly and Glu Gly, respectively, upon administration and uptake by cells. Accordingly, a peptide compound useful in a composition or method of the invention that comprises an amino acid sequence comprising one or more asparagine and/or glutamine residues also provides a disclosure of a corresponding peptide compound in which aspartate and/or glutamate are substituted for asparagine and/or glutamine residues, respectively. and vice versa.

Biological and Biochemical Activities

The peptide compounds useful in the compositions and methods of the invention have the ability to upregulate SOD and/or CAT, as well as activate and upregulate AP-1 in cells and tissues, especially mammalian cells, provided the cells contain at least one functional gene encoding a SOD or CAT protein. A functional gene is one, which not only encodes the particular enzyme, but also provides the necessary genetic information within and without the coding sequence so that transcription of the gene can occur and so that the mRNA transcript can be translated into a functioning gene product.

Certain preferred peptide compounds described herein are able to upregulate both SOD and CAT, assuming that functional genes for both enzymes are present in the cells of interest. Advantageously, upregulation of SOD and CAT together provide enhanced efficacy in detoxifying undesired ROS and free radicals. Without wishing to be bound by theory, when the level of SOD protein increases as a result of SOD upregulation, it is believed that superior antioxidative efficacy is achieved when there is also an increase in CAT levels. Upregulation of a gene for CAT increases the capacity to neutralize and detoxify the additional hydrogen peroxide and other ROS or free radicals that can be generated by enhanced SOD activity. The peptide compounds described herein having both SOD and CAT upregulation activity provide cells and tissues with a full complement of enhanced antioxidative enzyme activity to detoxify ROS and free radicals. For example, contacting mammalian cells in tissue culture with a peptide compound described herein having both SOD and CAT upregulation activity typically results in at least about a 2-fold (and in increasing order of preference, at least about a 3-fold, 4-fold, and a 6 to 8-fold) increase in the levels of SOD and CAT mRNA transcripts and about a 2-fold (and in increasing order of preference, at least about a 3-fold, 4-fold, 6-fold, 8-fold, 10-fold and a 12- to 14-fold) increase in the levels of SOD and CAT protein, as detected by immunoblotting and compared to untreated cells. Such increase in SOD and CAT gene expression levels provides a cell with a significantly enhanced capability for detoxifying ROS and free radicals without adverse effects.

Expression of genes encoding SOD, CAT, and AP-1 can be measured by a variety of methods. Standard enzymatic assays are available to detect levels of SOD and CAT in cell and tissue extracts or biological fluids (Fridovich, *Adv. Enzymol.*, 41:35-97 (1974); Beyer & Fridovich, *Anal. Biochem.*, 161: 559-566 (1987)). In addition, antibodies to SOD, CAT, and AP-1 are available or readily made. Using such antibodies specific for each protein, standard immunoblots (e.g., Western blots) and other immunological techniques can be used to measure levels of SOD and CAT in various mixtures, cell extracts, or other sample of biological material. Provided there is no evidence of a defect in the translation machinery of the cells of interest, the levels of expression of genes encoding SOD, CAT, and AP-1 can also be measured by detecting levels of mRNA transcripts using standard Northern blot or standard polymerase chain reaction (PCR) methods for measuring specific mRNA species (e.g., RT-PCR). In addition, activation and translocation of AP-1 to nuclei can be determined using a standard electrophoretic mobility shift assay (EMSA) in which the amount of AP-1 protein present in cell nuclei is detected by its ability to form a complex with a DNA probe molecule containing a specific DNA sequence for a promoter/enhancer region of a eukaryotic gene, which is known to be bound by AP-1. Typically, the AP-1 protein-DNA complex migrates with a slower mobility than unbound DNA. The AP-1 transcription factor complex is formed by the association of other factors, such as c-Jun and c-Fos, with a DNA molecule containing an AP-1 recognition sequence or site. The presence of AP-1 in a mixture or sample is then detected by the formation of such protein-DNA molecular complexes, which result in an observable shift in the electrophoretic mobility from the position of the uncomplexed DNA in a gel.

Other preferred peptide compounds useful in the compositions and methods of the invention are able to upregulate levels of the AP-1 transcription factor. For example, contacting mammalian cells in tissue culture with peptide compounds described herein typically results in at least about a 2-fold and, in order of increasing preference, at least about a 6-fold, 8-fold, 10-fold, 12-fold, 14-fold, 16-fold, 18-fold, and 20- to 60-fold increase in the level of AP-1 protein, as determined by EMSA. Such upregulation of AP-1 gene expression can result in an enhanced AP-1 dependent gene expression.

Therapeutic and Prophylactic Applications

The peptide compounds of the invention upregulate SOD and/or CAT in cells and tissues of animals, such as humans and other mammals. Preferably, the peptides of this invention upregulate both SOD and CAT. As noted above, SOD and CAT comprise components of the body's major enzymatic antioxidative activities that are able to detoxify ROS and free radicals by reducing such molecules to less reactive and less harmful compounds. The contribution of ROS and other free radicals to the progression of various disease states and side effects of drugs is now well known.

For example, elevated levels of ROS and free radicals are known to be generated in cells and tissues during reperfusion after an ischemic event. Such increased levels of ROS and free radicals can cause considerable damage to an already stressed or debilitated organ or tissue. The peptide compounds of this invention, which upregulate SOD and/or CAT, may be used to treat reperfusion injuries that occur in diseases and conditions such as stroke, heart attack, or renal disease and kidney transplants. If the ischemic event has already occurred as in stroke and heart attack, a peptide compound described herein may be administered to the individual to detoxify the elevated ROS and free radicals already present in the blood and affected tissue or organ. Alternatively, if the ischemic event is anticipated as in organ transplantation, then peptide compounds described herein may be administered prophylactically, prior to the operation or ischemic event.

Although a major application is in the treatment of ischemia-reperfusion injury, the peptide compounds described herein may be used to treat any disease or condition associated with undesirable levels of ROS and free radicals or to prevent any disease, disorder or condition caused by undesirable levels of ROS and free radicals. According to the invention, the peptide compounds described herein may also be administered to provide a therapeutic or prophylactic treatment of elevated ROS and other free radicals associated with a variety of other diseases and conditions, including, but not limited to, oxygen toxicity in premature infants, burns and physical trauma to tissues and organs, septic shock, polytraumatious shock, head trauma, brain trauma, spinal cord injuries, Parkinson's disease, amyotrophic lateral sclerosis (ALS), Alzheimer's disease, age-related elevation of ROS and free radicals, senility, ulcerative colitis, human leukemia and other cancers, Down syndrome, arthritis, macular degeneration, schizophrenia, epilepsy, radiation damage (including UV-induced skin damage), and drug-induced increase in ROS and free radicals.

A progressive rise of oxidative stress due to the formation of ROS and free radicals occurs during aging (see, e.g., Mecocci, P. et al., *Free Radic. Biol. Med.*, 28: 1243-1248 (2000)). This has been detected by fording an increase in the formation of lipid peroxidates in rat tissues (Erdincler, D. S., et al., *Clin. Chim. Acta*, 265: 77-84 (1997)) and blood cells in elderly human patients (Congi, F., et al., *Presse. Med.*, 24: 1115-1118 (1995)). A recent review (Niki, E., *Intern. Med.*, 39: 324-326 (2000)) reported that increased tissue damage by ROS and free radicals could be attributed to decreased levels of the antioxidative enzymes SOD and CAT that occurs during aging. For example, transgenic animals, generated by inserting extra SOD genes into the genome of mice were found to have decreased levels of ROS and free radical damage. Such animals also had an extended life span. More recent evidence indicated that administration of a small manganese porphyrin compound, which mimics SOD activity, led to a 44% extension of life span of the nematode worm *Caenorhabditis elegans* (S. Melow, et al., *Science*, 289: 1567-1569 (2000)). Accordingly, the peptide compounds described herein, which are able to upregulate expression of SOD and/or CAT genes to produce increased levels of antioxidative enzymes, are also well suited for use in methods of preventing and/or counteracting increased tissue damage and decreased life expectancy due to elevated levels of ROS and free radicals that accompany the aging process.

A variety of drugs in current therapeutic use produce tissue-specific toxic side effects that are correlated with an elevation in the levels of ROS and other free radicals. Such drugs include neuroleptics, antibiotics, analgesics, and other classes of drugs. The tissues affected by such drug-induced toxicities can include one or more of the major organs and tissues, such as brain, heart, lungs, liver, kidney, and blood.

One of the most dangerous side effects of a drug has been reported for the neuroleptic, clozapine, which was the first drug with major potential as an anti-schizophrenic therapeutic activity (see, Somani et al., In *Oxidants, Antioxidants And Free Radicals* (S. I. Baskin And H. Salem, eds.) (Taylor And Francis, Washington D.C., 1997), pages 125-136). Approximately 1-2% of clozapine-treated patients develop agranulocytosis, which is correlated with the production of ROS (Fischer et. al., *Molecular Pharm.*, 40:846-853, 1991). According to the invention, a peptide compound as described herein is administered to clozapine-treated patients to upregulate the SOD and/or CAT, which counteracts the undesirable and harmful increase in ROS and other free radicals and, thereby, reduces the risk of developing agranulocytosis.

Another side effect of schizophrenic patients receiving neuroleptics is Tardive dyskinesia, which is a debilitating disease manifested by various uncontrollable oral, facial, and/or trunk movements. Many patients, especially veterans in hospital, suffer permanent disability from this unfortunate, drug-induced disease. Previous studies on Tardive dyskinesia were focused on the loss of dopamine neurons (see, for example, Morganstern and Glazer, *Arch. Gen. Psychiatr.*, 50: 723-733 (1993)). However, more recent studies have demonstrated that the primary defect in brains of such patients is the overproduction of the excitotoxic amino acid glutamate in the presynaptic input to the striatal dopaminergic neurons. Notably, this overproduction of glutamate produces excitotoxic effects on dopamine cells by causing a high increase in ROS and free radicals (see, Tsai et al., *Am. J. Psychiatr.*, 155: 1207-1253 (1998)). Accordingly, the peptide compounds of this invention may be administered to patients receiving neuroleptics to upregulate SOD and/or CAT and thereby provide the enhanced antioxidative activities to counteract the oxidative effects of the elevated levels of ROS and free radicals.

According to the methods of the invention, peptide compounds described herein may be administered to an individual before, contemporaneously with, or after administration of a therapeutic drug whose use has been correlated with the undesirable side effect of elevation in the levels of ROS and other free radicals. Such drugs include, but are not limited to those listed in Table 1 (see, Somani et al., 1997), which also lists any known manifested toxicity or side effect.

TABLE 1

| DRUG | ROS or Reactive Free Radical or Toxic Result | Toxicity |
| --- | --- | --- |
| clozapine | ROS and free radicals | agranulocytosis |
| doxorubin (anthrcyclines) | superoxide anion, hydroxyl radical | cardiac |
| bleomycin | superoxide anion | pulmonary |
| mytomycin | free radical | |
| cisplatin | probably free radical | nephrotoxicity, otototoxicity |

TABLE 1-continued

| DRUG | ROS or Reactive Free Radical or Toxic Result | Toxicity |
|---|---|---|
| BCNU (carmustine) | methyl radical | neurotoxicity |
| procarbazine | free radical | neurotoxicity |
| acetaminophen | reactive intermediate metabolites of drug | hepatic |
| isoniazid | free radical | hepatic |
| ethanol | α-hydroxy ethyl radical | hepatic, neurotoxicity |
| physostigmine | eseroline to catechol to quinones | neurotoxicity |
| quinones | reactive metabolites of drug | neurotoxicity |
| morphine | covalent binding reactions | neurotoxicity |
| nitrofurantoin | oxidant | pulmonary |
| paraquat | oxidant | pulmonary |
| parathion | reactive metabolites of drug | neruotoxicity |
| carbon tetrachloride (CCl$_4$) | trichloromethyl radical | hepatic |
| polycyclic aromatic hydrocarbons | reactive epoxides | hepatic |
| nitrofurazone | ROS and free radicals | pulmonary |
| metronidazole | ROS and free radicals | pulmonary |
| 6-hydroxydopamine | ROS and free radicals | neurotoxin |
| 4-hydroxyanisole | free radicals | |
| etoposide (VP-16) | hydroxyl radicals | |
| benzidine | free radicals | bladder carcinogen |
| aminopyrine | free radicals | agranulocytosis |
| clozaril | free radicals | agranulocytosis |
| phenylhydrazine | ROS and free radicals | hemolytic anemia |
| 3-methylindole | free radicals | pulmonary |
| probucol | free radicals | |
| ferrous sulfate | hydroxyl radicals | iron overload |
| methimazole | free radicals | |
| chloroprazine | free radicals | phototoxicity, photoallergy |
| salicylanilides | free radicals | photoallergy |
| mitoxantrone | free radicals | |
| daunomycin | ROS and free radicals | cardiotoxicity |

Pharmaceutical Applications

Pharmaceutical compositions of this invention comprise any of the peptide compounds of the present invention, and pharmaceutically acceptable salts thereof, with any pharmaceutically acceptable ingredient, excipient, carrier, adjuvant or vehicle.

Pharmaceutical compositions of this invention can be administered to mammals, including humans, in a manner similar to other therapeutic, prophylactic, or diagnostic agents, and especially therapeutic hormone peptides. The dosage to be administered, and the mode of administration will depend on a variety of factors including age, weight, sex, condition of the patient, and genetic factors, and will ultimately be decided by the attending physician or veterinarian. In general, dosage required for diagnostic sensitivity or therapeutic efficacy will range from about 0.001 to 25.0 µg/kg of host body mass.

Pharmaceutically acceptable salts of the peptide compounds of this invention include, for example, those derived from pharmaceutically acceptable inorganic and organic acids and bases. Examples of suitable acids include hydrochloric, hydrobromic, sulfuric, nitric, perchloric, fumaric, maleic, malic, pamoic, phosphoric, glycolic, lactic, salicylic, succinic, toluene-p-sulfonic, tartaric, acetic, citric, methanesulfonic, formic, benzoic, malonic, naphthalene-2-sulfonic, tannic, carboxymethyl cellulose, polylactic, polyglycolic, and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N—(C$_{1-4}$ alkyl)$_4$$^+$ salts.

This invention also envisions the "quaternization" of any basic nitrogen-containing groups of a peptide compound disclosed herein, provided such quaternization does not destroy the ability of the peptide compound to upregulate expression of genes encoding SOD and CAT, and, where desired, AP-1. Such quaternization may be especially desirable where the goal is to use a peptide compound containing only positively charged residues. As noted above, in a most preferred embodiment of the invention, when charged amino acid residues are present in a peptide compound described herein, they are either all basic (positively charged) or all acidic (negatively) which prevents formation of cyclic peptide compounds during storage or use. Typically, cyclic forms of the peptide compounds are inactive and potentially toxic. Thus, a quaternized peptide compound is a preferred form of a peptide compound containing basic amino acids. Even more preferred is the quaternized peptide compound in which the carboxy terminal carboxyl group is converted to an amide to prevent the carboxyl group from reacting with any free amino groups to form a cyclic compound. Any basic nitrogen can be quaternized with any agent known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization or acids such as acetic acid and hydrochloric acid.

It should be understood that the peptide compounds of this invention may be modified by appropriate functionalities to enhance selective biological properties, and in particular the ability to upregulate SOD and/or CAT and/or AP-1. Such modifications are known in the art and include those, which increase the ability of the peptide compound to penetrate or being transported into a given biological system (e.g., brain, central nervous system, blood, lymphatic system), increase oral availability, increase solubility to allow administration by injection, alter metabolism of the peptide compound, and alter the rate of excretion of the peptide compound. In addition, the peptide compounds may be altered to a pro-drug form such that the desired peptide compound is created in the body of the patient as the result of the action of metabolic or other biochemical processes on the pro-drug. Such pro-drug forms typically demonstrate little or no activity in in vitro assays. Some examples of pro-drug forms may include ketal, acetal, oxime, and hydrazone forms of compounds which contain ketone or aldehyde groups. Other examples of pro-drug forms include the hemi-ketal, hemi-acetal, acyloxy ketal, acyloxy acetal, ketal, and acetal forms.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered by a variety of routes or modes. These include, but are not limited to, parenteral, oral, intratracheal, sublingual, pulmonary, topical, rectal, nasal, buccal, sublingual, vaginal, or via an implanted reservoir. Implanted reservoirs may function by mechanical, osmotic, or other means. The term "parenteral", as understood and used herein, includes intravenous, intracranial, intraperitoneal, paravertebral, periarticular, periostal, subcutaneous, intracutaneous, intra-arterial, intramuscular, intra-articular, intrasynovial, intrasternal, intrathecal, and intralesional injection or infusion techniques. Such compositions are preferably formulated for parenteral administration, and most preferably for intravenous, intracranial, or intra-arterial administration. Generally, and particularly when administration is intravenous or intra-arterial, pharmaceutical compositions may be given as a bolus, as two or more doses separated in time, or as a constant or non-linear flow infusion.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in *Pharmacoplia Halselica*.

The pharmaceutical compositions of this invention may be orally administered in any orally acceptable dosage form including, but not limited to, capsules, tablets, caplets, pills, aqueous or oleaginous suspensions and solutions, syrups, or elixirs. In the case of tablets for oral use, carriers, which are commonly used include lactose and corn starch. Lubricating agents, such as magnesium stearate, are also typically added. For oral administration in a capsule form, useful diluents include lactose and dried cornstarch. Capsules, tablets, pills and caplets may be formulated for delayed or sustained release.

When aqueous suspensions are to be administered orally, the peptide compound is advantageously combined with emulsifying and/or suspending agents. If desired, certain sweetening and/or flavoring and/or coloring agents may be added. Formulations for oral administration may contain 10%-95% active ingredient, preferably 25%-70%. Preferably, a pharmaceutical composition for oral administration provides a peptide compound of the invention in a mixture that prevents or inhibits hydrolysis of the peptide compound by the digestive system, but allows absorption into the blood stream.

The pharmaceutical compositions of this invention may also be administered in the form of suppositories for vaginal or rectal administration. These compositions can be prepared by mixing a compound of this invention with a suitable non-irritating excipient, which is solid at room temperature but liquid at body temperature and therefore will melt in relevant body space to release the active components. Such materials include, but are not limited to, cocoa butter, beeswax and polyethylene glycols. Formulations for administration by suppository may contain 0.5%-10% active ingredient, preferably 1%-2%.

Topical administration of the pharmaceutical compositions of this invention may be useful when the desired treatment involves areas or organs accessible by topical application, such as in wounds or during surgery. For application topically, the pharmaceutical composition may be formulated with a suitable ointment containing the active components suspended or dissolved in a carrier. Carriers for topical administration of the peptide compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the peptide compounds suspended or dissolved in a pharmaceutically suitable carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical composition may be formulated for topical or other application as a jelly, gel, or emollient, where appropriate. The pharmaceutical compositions of this invention may also be topically applied to the lower intestinal tract by rectal suppository formulation or in a suitable enema formulation. Topical administration may also be accomplished via transdermal patches. This may be useful for maintaining a healthy skin tissue and restoring oxidative skin damage (e.g., UV- or radiation-induced skin damage).

The pharmaceutical compositions of this invention may be administered nasally, in which case absorption may occur via the mucus membranes of the nose, or inhalation into the lungs. Such modes of administration typically require that the composition be provided in the form of a powder, solution, or liquid suspension, which is then mixed with a gas (e.g., air, oxygen, nitrogen, etc., or combinations thereof) so as to generate an aerosol or suspension of droplets or particles. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Pharmaceutical compositions of the invention may be packaged in a variety of ways appropriate to the dosage form and mode of administration. These include but are not limited to vials, bottles, cans, packets, ampoules, cartons, flexible containers, inhalers, and nebulizers. Such compositions may be packaged for single or multiple administrations from the same container. Kits, of one or more doses, may be provided containing both the composition in dry powder or lyophilized form, as well an appropriate diluent, which are to be combined shortly before administration. The pharmaceutical composition may also be packaged in single use pre-filled syringes, or in cartridges for auto-injectors and needleless jet injectors.

Multi-use packaging may require the addition of antimicrobial agents such as phenol, benzyl alcohol, meta-cresol, methyl paraben, propyl paraben, benzalconium chloride, and benzethonium chloride, at concentrations that will prevent the growth of bacteria, fungi, and the like, but be non-toxic when administered to a patient.

Consistent with good manufacturing practices, which are in current use in the pharmaceutical industry and which are well known to the skilled practioner, all components contacting or comprising the pharmaceutical agent must be sterile and periodically tested for sterility in accordance with industry norms. Methods for sterilization include ultrafiltration, autoclaving, dry and wet heating, exposure to gases such as ethylene oxide, exposure to liquids, such as oxidizing agents, including sodium hypochlorite (bleach), exposure to high energy electromagnetic radiation, such as ultraviolet light, x-rays or gamma rays, and exposure to ionizing radiation. Choice of method of sterilization will be made by the skilled practioner with the goal of effecting the most efficient sterilization that does not significantly alter a desired biological function, i.e., the ability to upregulate SOD, CAT, or AP-1, of the pharmaceutical agent in question. Ultrafiltration is a preferred method of sterilization for pharmaceutical compositions that are aqueous solutions or suspensions.

Details concerning dosages, dosage forms, modes of administration, composition and the like are further discussed in a standard pharmaceutical text, such as *Remington's Pharmaceutical Sciences,* 18th ed., Alfonso R. Gennaro, ed. (Mack Publishing Co., Easton, Pa. 1990), which is hereby incorporated by reference.

As is well known in the art, structure and biological function of peptides are sensitive to chemical and physical environmental conditions such as temperature, pH, oxidizing and reducing agents, freezing, shaking and shear stress. Due to this inherent susceptibility to degradation, it is necessary to ensure that the biological activity of a peptide compound used as a pharmaceutical agent be preserved during the time that the agent is manufactured, packaged, distributed, stored, prepared and administered by a competent practitioner. Many technical approaches have been developed to stabilize pharmaceutical proteins so as to preserve their biological potency and efficacy, and such stabilizing techniques may be applied to peptide compounds of the compositions and methods of the invention, including:

a) Freeze-drying and lyophilization (refer to Carpenter et al., *Pharm. Res.,* 14(8): 969 (1997), incorporated by reference);

b) Addition of "stabilizers" to the aqueous solution or suspension of the peptide or protein. For example, U.S. Pat. No. 5,096,885 discloses addition of glycine, mannitol, pH buffers, and the non-ionic surfactant polysorbate 80 to human growth hormone as means to stabilize the protein during the process of filtration, vial filling, and cold storage or lyophilization; U.S. Pat. No. 4,297,344 discloses stabilization of coagulation factors H and VIII, antithrombin III and plasminogen against heat by adding selected amino acids and a carbohydrate; U.S. Pat. No. 4,783,441 discloses a method for prevention of denaturation of proteins such as insulin in aqueous solution at interfaces by the addition of surface acting substances, within a particular pH range; and U.S. Pat. No. 4,812,557 discloses a method of stabilizing interleukin-2 using human serum albumin;

c) Freeze/thaw methods wherein the peptide compound is mixed with a cryoprotectant and stored frozen at very low temperatures (e.g., −70° C.);

d) Cold, non-frozen storage (e.g., less than 4° C.), optionally with a cryoprotectant additive such as glycerol;

e) Storage in a vitrified, amorphous state, e.g., as described in U.S. Pat. No. 5,098,893;

f) Storage in a crystalline state; and g) Incorporation into liposomes or other micelles.

Natural Source, Purified Compositions and Dietary Supplements

The invention also provides compositions and methods of making such compositions for use as dietary supplements (also referred to as "nutraceuticals") comprising a natural source purified composition obtained from an organism (i.e., animal, plant, or microorganism), which purified composition contains an endogenous peptide compound described herein, which upregulates expression of one or more genes encoding an antioxidative enzyme, such as SOD and/or CAT in cells or tissues. Although peptide compounds of the invention may be obtained in highly purified form from some natural sources, the level of such peptide compounds in natural materials may be quite low or even present in only a trace detectable amount, even in compositions purified from such natural sources. Accordingly, to obtain useful quantities of pure peptide compounds, it is usually more economical to synthesize the peptide compounds described herein using in vitro automated peptide synthesis protocols. However, purified preparations from natural sources that contain even trace amounts of a compound capable of upregulating an antioxidative enzyme (such as SOD and/or CAT) may be useful in manufacturing products for sale in the oral dietary supplements market. Accordingly, dietary supplement compositions of the invention may further comprise an exogenously provided peptide compound described herein that upregulates expression of one or more genes encoding an antioxidative enzyme, such as SOD and/or CAT. Preferred natural sources of purified compositions used in making dietary supplements of the invention include green velvet antler from a ruminant, such as deer or elk, and various plant tissue, such as roots, stems, leaves, flowers, herbal mixtures, and teas. A preferred natural plant source useful in preparing dietary supplements of the invention is wuzi yanzong herbal mixture. Wuzi yanzong herbal mixture has been reported to confer on individuals a number of beneficial effects, including elevation of levels of certain antioxidative enzymes such as SOD and blood glutathione peroxidase, that make it a desirable natural source for use in manufacturing marketable dietary supplements of the invention (see, e.g., abstracts from Huang et al., *Chung Kuo Chung Yao Tsa Chih,* 16: 414-416, 447 (1991); Wang et al., *Chung Kuo Chung Hsi I Chieh Ho Tsa Chih,* 12: 23-25, 5 (1992); Wang et al., *Chung Kuo Chung Hsi I Chieh Ho Tsa Chih,* 13: 349-351, 325-326 (1993); Li et al., *Chung Kuo Chung Yao Tsa Chih,* 19: 300-302 (1994)).

Dietary supplement formulations of the invention may comprise a natural source purified composition comprising an endogenous peptide compound described herein. Other dietary supplement formulations of the invention are compositions which comprise a natural source purified composition containing an endogenous peptide compound, which is combined with one or more exogenously provided peptide compounds described herein. An advantage of this latter type of formulation is that a sufficient amount of an exogenously provided peptide compound described herein may be combined with the natural source purified composition to form a dietary supplement composition that produces a desirable level or range of levels of upregulated antioxidative enzymes in an individual that takes or is administered the dietary supplement. Accordingly, dietary supplement compositions of the invention may contain one or more different peptide compounds described herein as an endogenous peptide compound from a natural source purified composition as well as, if so formulated, an exogenously provided peptide compound described herein. According to the invention, dietary supplements may comprise an endogenous peptide compound and an exogenously provided peptide compound that are the same or different peptide compounds.

Preferred dietary supplements of the invention comprise a peptide compound comprising the formulas:

$R_1$ Xaa$_1$ Gly Xaa$_2$ Xaa$_3$ Xaa$_4$ Xaa$_5$ Xaa$_6$ $R_2$, (SEQ ID NO: 3)

wherein Xaa$_1$ and Xaa$_2$ are, independently, aspartic acid or asparagine; $R_1$ is absent or is an amino terminal capping group of the peptide compound; Xaa$_3$ is absent or Gly; Xaa$_4$ is absent, Asp, or Phe; Xaa$_5$ is absent, Ala, or Phe; Xaa$_6$ is absent or Ala; $R_2$ is absent or is a carboxy terminal capping group of the peptide compound; and wherein the peptide compound upregulates expression of a gene encoding an antioxidative enzymes; and $R_1$ Xaa$_1$ Xaa$_2$ Xaa$_3$ $R_2$, wherein Xaa$_1$ is Asp, Asn, Glu, Gln, Thr, or Tyr; Xaa$_2$ is absent or any amino acid; Xaa$_3$ is Asp, Asn, Glu, Thr, Ser, Gly, or Leu; $R_1$ is absent or is an amino terminal capping group; $R_2$ is absent or is a carboxy terminal capping group; and wherein the peptide compound upregulates expression of a gene encoding an antioxidative enzyme.

Preferred dietary supplement compositions of the invention may comprise one or more peptide compounds that upregulate expression of at least one gene encoding an antioxidative enzyme selected from the group consisting of:

Gln Tyr Lys Leu Gly Ser Lys Thr Gly Pro Gly Gln, (SEQ ID NO: 1)

Gln Thr Leu Gln Phe Arg, (SEQ ID NO: 2)

Glu Thr Leu Gln Phe Arg, (SEQ ID NO: 13)

Gln Tyr Ser Ile Gly Gly Pro Gln, (SEQ ID NO: 14)

Ser Asp Arg Ser Ala Arg Ser Tyr, (SEQ ID NO: 15)

Ser Lys Met Thr Leu Thr Gln Pro, (SEQ ID NO: 12)

Met Thr Leu Thr Gln Pro, (SEQ ID NO: 13)

Asp Gly Asp Gly Asp Phe Ala Ile Asp Ala Pro Glu, (SEQ ID NO: 16)

Asp Gly Asp Gly Asp Phe Ala, (SEQ ID NO: 6)

Asp Gly Asp Gly Asp, (SEQ ID NO: 4)

Asn Gly Asn Gly Asp Phe Ala, (SEQ ID NO: 8)

Asn Gly Asn Gly Asp, (SEQ ID NO: 17)

Asp Gly Asn Gly Asp Phe Ala, (SEQ ID NO: 7)

Asp Gly Asn Gly Asp, (SEQ ID NO: 18)

Asn Gly Asp Gly Asp Phe Ala, (SEQ ID NO: 9)

Asn Gly Asp Gly Asp, (SEQ ID NO: 19)

Asn Gly Asp Gly, (SEQ ID NO: 20)

Asp Gly Asp Gly Phe Ala, (SEQ ID NO: 5)

Asn Gly Asn Gly Phe Ala, (SEQ ID NO: 21)

Asp Gly Asn Gly Phe Ala, (SEQ ID NO: 22)

Asn Gly Asp Gly Phe Ala, (SEQ ID NO: 23)

Asp Gly Asp, Asn Gly Asn, Asp Gly Asn, Asn Gly Asp, Asn Ser Thr, Phe Asp Gln, Met Thr Leu, Met Thr Asp, Met Thr Asn, Met Thr Thr, Met Thr Glu, Met Thr Gln, Thr Val Ser, Leu Thr Gln, Leu Thr Gly, Leu Thr Tyr, Asp Gly, Asn Gly, Glu Gly, Gln Gly, Glu Ala, Gln Ala, Gln Gly, Asp Ala, and Asn Ala. A particularly preferred peptide compound useful in manufacturing dietary supplement formulations of the invention comprises the amino acid sequence Asp Gly.

Dietary supplement compositions of the invention may also comprise one or more peptide compounds described herein that have an amino terminal capping group and/or a carboxy terminal capping group. Preferably, the amino terminal capping group is selected from a group consisting of a reduced or oxidized lipoic acid moiety (Lip), a glucose-3-O-glycolic acid (Gga) moiety, 1 to 6 lysine residues, 1 to 6 arginine residues, an acyl group having the formula $R_3$—CO—, where CO represents a carbonyl group and $R_3$ is a saturated or an unsaturated (mono- or polyunsaturated) hydrocarbon chain having from 1 to 25 carbons, and combinations thereof. Even more preferably, the amino terminal capping group is the acyl group that is an acetyl group, a palmitoyl group, or a docosahexaenoic acid group (DHA). In another preferred embodiment, a peptide compound present in a dietary supplement of the invention comprises a carboxy terminal capping group selected from the group consisting of a primary or secondary amine.

Compositions containing one or more endogenous peptide compounds described herein may be purified from a natural source using various methods and protocols available in the art, such as fractionation by centrifugation, concentration, gel filtration chromatography, organic solvent extraction, etc. Such methods are employed by those skilled in the art to obtain a composition purified from an original natural source, such as green velvet antler of deer, which is commercially available as a powder, or wuzi yanzong herbal mixture, which is commercially available as a dry or liquid herbal mixture. The desired purified composition will typically be enriched (more concentrated) for an endogenous peptide compound described herein. Such a purified composition may be marketed as an oral dietary supplement. Alternatively, a natural source purified compositions may also be combined with an exogenously provided, synthetically produced peptide compound described herein to produce a dietary supplement. Dietary supplement compositions of the invention may further contain other marketable ingredients of interest, such as lazaroids, vitamins, enzymes, and peptides purported to provide a benefit to health or well-being of the individual who ingests them. In addition, dietary supplement compositions of the invention may also comprise one or more binders, fillers, powders, silica, or other inert ingredients commonly used in the dietary supplements or pharmaceutical industries to make marketable forms of the supplement compositions, such as pills, capsules, lozenges, liquids, and syrups (see above section on pharmaceutical compositions). Unlike pharmaceuticals, however, the peptide compounds and other ingredients used to make a dietary supplement composition are typically not regulated or otherwise controlled by a federal regulatory agency.

Natural source purified compositions can be assayed for the presence of one or more peptide compounds, and the activity to upregulate expression of a gene encoding SOD and/or CAT assayed in vitro or in vivo in mammalian cells by any of the various methods described herein or their equivalents. Such analysis provides the information that enables the consistent manufacture of standardized lots of an oral dietary supplement product, which contains an appropriate amount of a peptide compound to provide the same or substantially the same lot to lot antioxidative activity to an individual who takes the supplement. The ability to consistently manufacture and deliver for sale lots of the same oral supplement product having a standardized amount of an ingredient of interest is highly desired in the dietary supplements market where product consistency can play a critical role in establishing consumer confidence and patronage for a particular product.

Additional aspects of the invention will be further understood and illustrated in the following examples. The specific parameters included in the following examples are intended to illustrate the practice of the invention and its various features, and they are not presented to in any way limit the scope of the invention.

EXAMPLES

Example 1

Synthesis of Representative Peptide Compounds

The following representative peptide compounds were synthesized by solid phase Merrifield synthesis (Merrifield, *J. Am. Chem. Soc.*, 85:2149-2154 (1963)):

```
CMX-9236D
                                        (SEQ ID NO: 26)
([DHA]-Lys Lys Asp Gly Asp Gly Asp

Phe Ala Ile Asp Ala Pro Glu),

CMX-9236
                                        (SEQ ID NO: 26)
(Lys Lys Asp Gly Asp Gly Asp Phe Ala Ile

Asp Ala Pro Glu),

CMX-11540
                                        (SEQ ID NO: 16)
([Lip]-Asp Gly Asp Gly Asp Phe Ala Ile

Asp Ala Pro Glu),

CMX-99661
                                         (SEQ ID NO: 5)
([Gga] Asp Gly Asp Gly Phe Ala),

CMX-99655
                                         (SEQ ID NO: 5)
([Ac] Asp Gly Asp Gly Phe Ala),

CMX-9960
                                         (SEQ ID NO: 5)
([Palm] Asp Gly Asp Gly Phe Ala),
```

```
-continued
CMX-9963
                                         (SEQ ID NO: 6)
([Ac]-Asp Gly Asp Gly Asp Phe Ala), CMX-9967
([Ac]-Asp Gly Asp), CMX-9901
                                        (SEQ ID NO: 27)
(Lys Lys Gln Tyr Lys Leu Gly Ser Lys Thr Gly Pro Gly Gln), CMX-8933
                                        (SEQ ID NO: 24)
(Lys Lys Glu Thr Leu Gln Phe Arg), CMX-9902
                                        (SEQ ID NO: 28)
(Lys Lys Asp Gly Asp Gly Asp Phe Ala), CMX-99658
                                         (SEQ ID NO: 2)
([Ac]-Gln Thr Leu Gln Phe Arg), (SEQ ID NO: 2)
Lys Lys Gln Thr Leu Gln Phe Arg, CMX-8933
                                        (SEQ ID NO: 24)
(Lys Lys Glu Thr Leu Gln Phe Arg), (described in U.S. Pat. No. 5,545,719)

CMX-1156
([Lip]-Thr Val Ser),

CMX-99647
([Ac] Thr Val Ser),

CMX-1152
(Asp Gly),
```

CMX-1159 ([Lip]-Asp Gly), and CMX-99672 (trifluoroacetic acid salt of dipeptide Asp Gly). Amino terminal capping groups are indicated by the bracketed groups "[DHA]-", "[Lip]-", and "[Ac]-", which represent an all cis-docasahexaenoic acid moiety, a lipoic acid moiety, and an acetyl moiety, respectively, attached by acylation to the α-amino group of the amino terminal amino acid residue of the indicated peptide compounds (Shashoua and Hesse, *Life Sci.* 58:1347-1357 (1996)).

The peptides were synthesized using standard procedures. Briefly, the peptides were synthesized using the solid phase Merrifield process (Merrifield, R. B., *J. Am. Chem. Soc.*, 85:2149-2154 (1963)). This method allows the synthesis of a peptide of a specific amino acid sequence bound on a polymeric resin. Each newly synthesized peptide was then released from the resin by treating with trifluoroacetic acid (TFA). The resultant trifluoroacetic acid peptide salt was purified by ether precipitation according to standard procedures (see, E. Groos and Meienhofer, In *The peptides analysis, synthesis, biology*, vol. 2, (Academic Press, New York 1983)).

For N-terminal substituted peptides (i.e., peptides containing an acyl amino terminal capping group), each peptide was synthesized with blocked side chains using solid phase Merrifield synthesis (see above). The bound peptide was then treated with an equimolar amount of an anhydride of one of the following acids: acetic acid, DHA, or lipoic acid, in the presence of 4-dimethylamino pyridine under argon atmosphere. The reaction was carried out for about three hours to obtain N-terminal coupling. Evidence of complete N-terminal coupling was obtained prior to peptide isolation. This was established by monitoring the ninhydrin staining properties of the resin bound peptides using standard procedures (E. Kaiser, et al., *Anal. Biochem.*, 34: 595-598 (1970)). The N-terminal coupled (capped) peptide molecule was then released from the resin by treatment with TFA and purified by precipitation with cold ether followed by HPLC using methanolic HCl (50:50) as the eluant. The final peptide products were white solids after lyophilization. Structures were confirmed by amino acid analyses, by migration as a single peak on HPLC, and molecular weight determinations by mass spectrometry. For most uses, it was essential to completely remove TFA from the peptide compound. This was achieved by repeated dissolution of the peptide in glacial acetic acid followed by concentration in vacuo in rotary evaporator. Complete absence of TFA was established by mass spectrometry.

Example 2

Upregulation of Superoxide Dismutase (SOD) and Catalase (CAT) in Mammalian Cells by Peptide Compounds CMX-9236, CMX-9963, and CMX-9967

Upregulation of SOD

The RT-PCR method (see, for example, Innis et al., *PCR Protocols: A Guide to Methods and Applications*, (Academic Press, San Diego, 1990)) was used to investigate the upregulation of the specific mRNA that codes for the enzyme superoxide dismutase (SOD).

Primary cortical cultures were obtained by growing newborn rat brain cortical cells in Delbecco's modified Eagle medium supplemented with 25 μg/ml of gentamycin and 10% fetal calf serum. The cells were isolated from the E-21 cortex of rat brain, plated at a density of $1 \times 10^5$ per ml and grown to confluence within four to five days in an atmosphere containing air and 5% $CO_2$ at 37° C. as described in Cornell-Bell et al., *Science,* 247: 470-473 (1990) and *Cell Calcium,* 12: 185-204 (1991). Cultures were grown in 20 ml flasks as a monolayer and then exposed to various concentrations of peptides for studies of the effects of peptides on upregulation of genes for SOD and CAT and on the transmigration of transcription factor AP-1 to cell nuclei.

Primary cultures of rat brain cortical cells were incubated with 100 ng/ml of peptide compound CMX-9236 for durations of 0 to 48 hours. mRNA was isolated from the cytoplasmic fraction of lysed cells according to standard methods (Angel et al., *Cell* 49:729-739, 1987). The RNA was incubated according to the RT-PCR protocol with two strands, 20 nucleotides long, one for the sense and one from the antisense strand. The sequences were selected to be unique for superoxide dismutase-1 (SOD-1), and to span one intron segment. These were demonstrated to be unique by the BLAST program system (*Nucl. Acids Res.* 25:3389-3402, 1997). The sequence of the two probe segments of the oligo dT segments for SOD are as follows: anti-sense strand, ATCCCAAT-CACTCCACAGGCCAAGC (SEQ ID NO:29), and sense strand, GAGACCTGGGCAATGTGACTGCTGG (SEQ ID NO:30). These span a sequence of 208 base pairs (bp) on the primary SOD sequence. The mixture was then treated with reverse transcriptase to obtain the cDNA according to standard PCR methods. The cDNA was then analyzed by electrophoresis and separated according to sequence lengths on a non-denaturing 5% polyacrylamide gel. The electrophoretically separated molecules were treated with ethidium bromide to stain double-stranded DNA fragments. These were visualized by ultraviolet illumination and photographed. The gels were then analyzed by a laser scanning fluorescence detector to quantitate the amount of messenger RNA for the extent of upregulation of SOD message and its time course of synthesis as a function of stimulation by CMX-9236. Similar methods of analysis were used for other peptides.

FIG. 1A shows the results of the electrophoresis. Each lane contained an internal marker for glyceraldehyde-3-phosphate dehydrogenase (GAPDH, 451 bp), a housekeeper marker to ensure that the same amount of RT-PCR cDNA product was actually loaded in each lane. The results show that after 3 hours of incubation with 100 ng/ml of CMX-9236, there was a 9-fold upregulation of SOD-1 mRNA transcripts. The gel also contained a positive control (Pos) in which cortical cell cultures were stimulated with 10 μg/ml of the peptide compound for 3 hours, showing a maximum development of SOD stimulation.

Figure 1B:
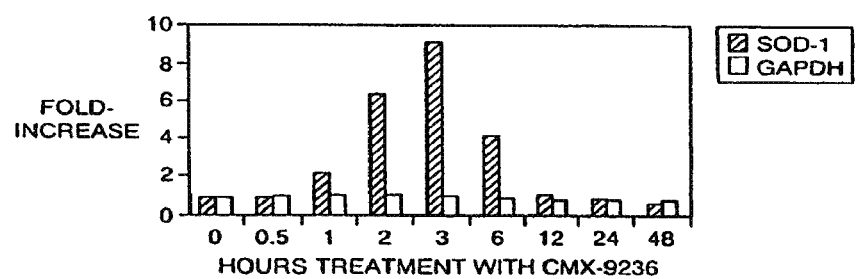

FIG. 1B shows a bar graph depicting quantitative analysis data of the upregulation of SOD mRNA. Note that within 3 hours, there is a 9-fold increase in upregulation of the mRNA with 100 ng/ml of peptide CMX-9236. This stimulation returns to control levels within 24 hours. The results demonstrate that CMX-9236 can upregulate the mRNA that codes for superoxide dismutase-1 (SOD-1). Filled bars indicate levels of SOD-1; open bars indicate levels of GAPDH.

Figure 2A:
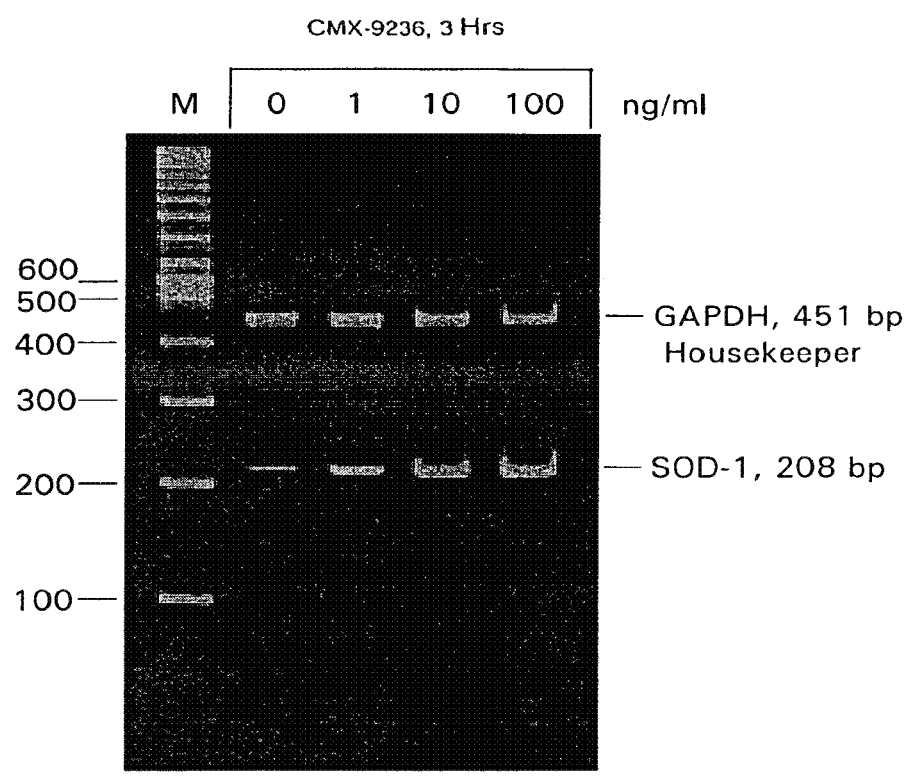
FIGS. 2A and 2B show that peptide compound CMX-9236 upregulated SOD-1 gene expression in rat primary myocyte cultures.
Figure 2B:
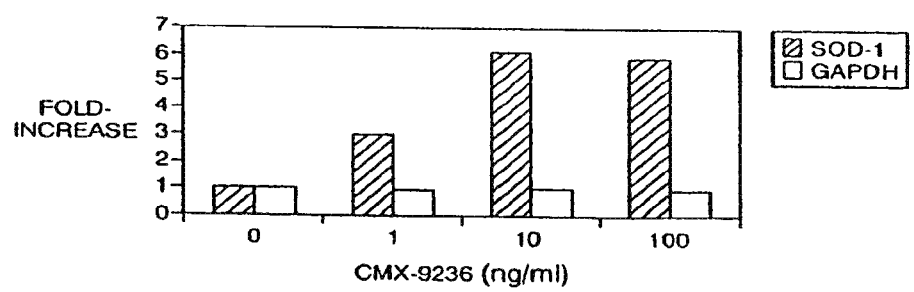

Similar RT-PCR experiments showed that cultures of rat primary myocytes upon stimulation with 1-100 ng/ml of CMX-9236 resulted in an enhanced production of mRNA coding for SOD-1. The amount of upregulation of SOD was 3-fold for the 1 ng/ml, and rose up to 6-fold at the 10-100 ng/ml (FIGS. 2A and 2B). FIG. 2A shows the dose-response data for the effect of CMX-9236 on the pattern of mRNA synthesis in primary myocyte cultures after a 3-hour incubation. The presence of a band at the region of the gel corresponding to 208 base pairs indicates that SOD is upregulated. FIG. 213 shows a bar graph depicting quantitative analysis data indicating that the 10 ng/ml and 100 ng/ml doses of CMX-9236 produced an upregulation of about 6-fold in the level of SOD-1 transcripts. Filled bars indicate fold-increase in levels of SOD-1 transcripts; open bars indicate fold-increase in levels of GAPDH transcripts.

The results shown in FIGS. 1A, 1B, 2A, and 2B demonstrated that the peptide compound is capable of upregulating SOD-1 mRNA in at least two different tissues, i.e., brain and muscle.

Translation of SOD mRNA to SOD-1 Protein

Figure 3A:
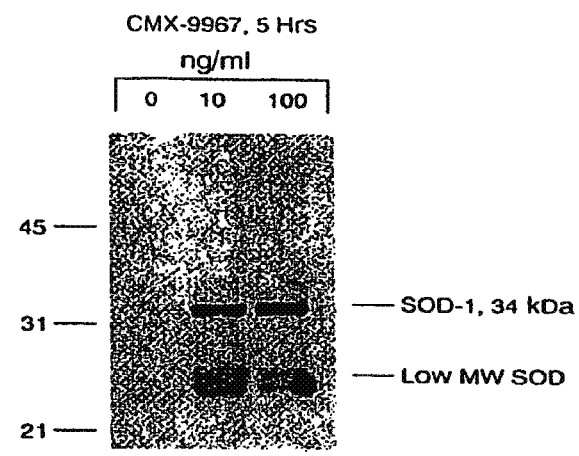
FIGS. 3A and 3B show that peptide compound CMX-9967 upregulated the synthesis of SOD-1 protein in rat brain primary cortical cultures incubated with 0, 10, and 100 ng/ml of the peptide compound for 5 hours.

Additional evidence for increased synthesis of SOD within stimulated cells was obtained by studies of the effect of representative peptide compounds on the pattern of protein synthesis. Time course and dose response studies on rat brain cortical cell cultures showed that the level of immunoreactive (i.e., anti-SOD antibody reactive) proteins that were synthesized in the cytoplasm increased as a function of treatment with the peptide compound CMX-9967. Rabbit polyclonal antibodies (Rockland, Inc., Gilbertville, Pa.) in a Western blot assay showed a dose-dependent antibody binding to the electrophoretically separated cytoplasmic SOD proteins on polyacrylamide gels (FIG. 3A). Specifically, FIG. 3A shows a Western blot containing a band migrating at 34 lcDa (the molecular weight of SOD-1), and two lower molecular weight bands corresponding to smaller components recognized by the anti-SOD-1 antibody in cells from cultures incubated for 5 hours in the presence of 10 and 100 ng/ml of the CMX-9967 peptide.

Figure 3B:
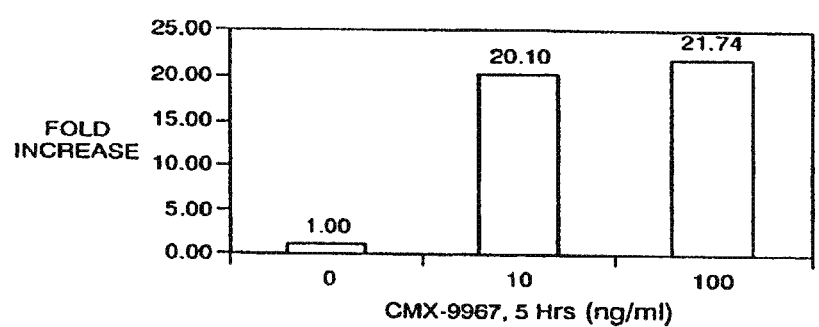

FIG. 3B shows a bar graph of the quantitative analysis of the data plotted as fold-increase in SOD-1 protein as a function of dose of the CMX-9967 peptide. At least a 20-fold increase in the intensity of antibody binding occurred at the position of the cytoplasmic SOD-1 (mol. wt. 34,000 daltons) and its lower molecular weight analogue in cells treated for 5 hours with 10 and 100 ng/ml of CMX-9967. This represents a large increase as compared to the published data for transgenic mice with an extra SOD gene insert where at most a 50% increase in SOD was detected (Murakami et al., *Stroke*, 28: 1797-1804 (1997); Ceballos-Picot, *CR Seances Soc. Biol. Fil.*, 187: 308-323 (1993)). The DNA sequence of such mice contains a second SOD gene insert. Thus, these data indicate that a peptide compound of the invention can upregulate mRNA for SOD-1, which is translated into a protein that has the same immunoreactive properties as SOD.

Upregulation of mRNA for Catalase (CAT)

Peptide compounds of the invention may also upregulate mRNA for catalase (CAT). Experiments using the RT-PCR methods to detect upregulation of CAT mRNA in primary rat cortical brain cultures treated with various representative peptide compounds, i.e., CMX-9236, CMX-9963, and CMX-9967. The catalase probe duplex consisted of a sense primer having the sequence GCCCGAGTCCAGGCTCTTCTG-GACC (SEQ ID NO:31) and antisense primer having the sequence TTGGCAGCTATGTGAGAGCCGGCCT (SEQ ID NO:32) flanking a 95 bp region of the CAT DNA.

Figure 4A:
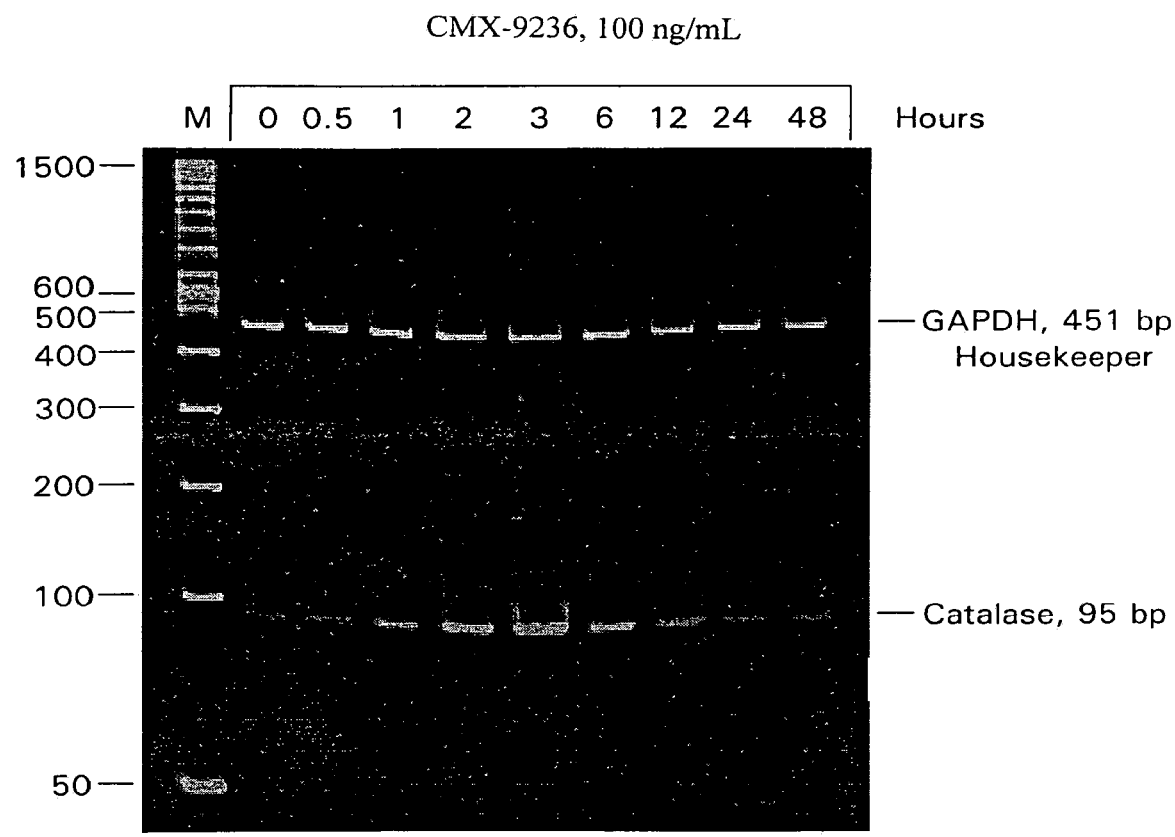
FIGS. 4A and 4B show that peptide compound CMX-9236 upregulated catalase mRNA transcripts of the catalase gene in primary rat cortical cell cultures incubated with the peptide compound CMX-9236 (100 ng/ml) for varying amounts of time (0-48 hours) as measured by the RT-PCR method.
Figure 4B:
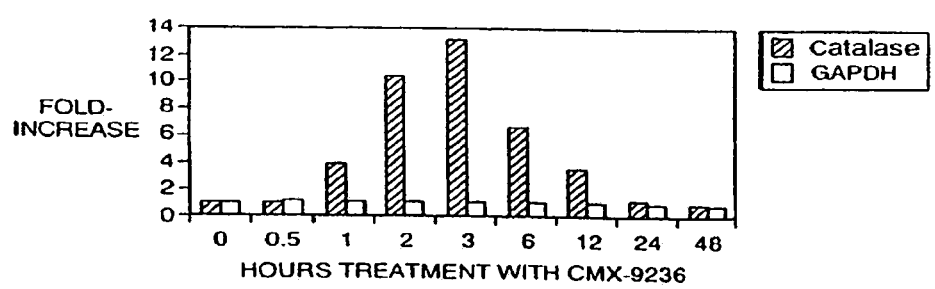

Primary rat brain cortical cell cultures were incubated with 100 ng/ml of the peptide compound CMX-9236 for 0, 0.5, 1, 2, 3, 6, 12, 24, and 48 hours. The results of the RT-PCR method are shown in FIGS. 4A and 4B. FIG. 4A shows a gel of RT-PCR products. The upregulation of CAT mRNA was maximal at 3 hours after the addition of the peptide compound, and it decreased back to control levels at 48 hours. GAPDH was the internal standard in these experiments. FIG. 4B shows a bar graph of the quantitative analysis of the data plotted as fold-increase as a function of hours of treatment. A 13-fold increase in CAT mRNA levels was observed (over control) of CAT mRNA occurred when primary rat brain cortical cultures were incubated with 100 ng/ml of CMX-9236 for 3 hours.

Figure 5A:
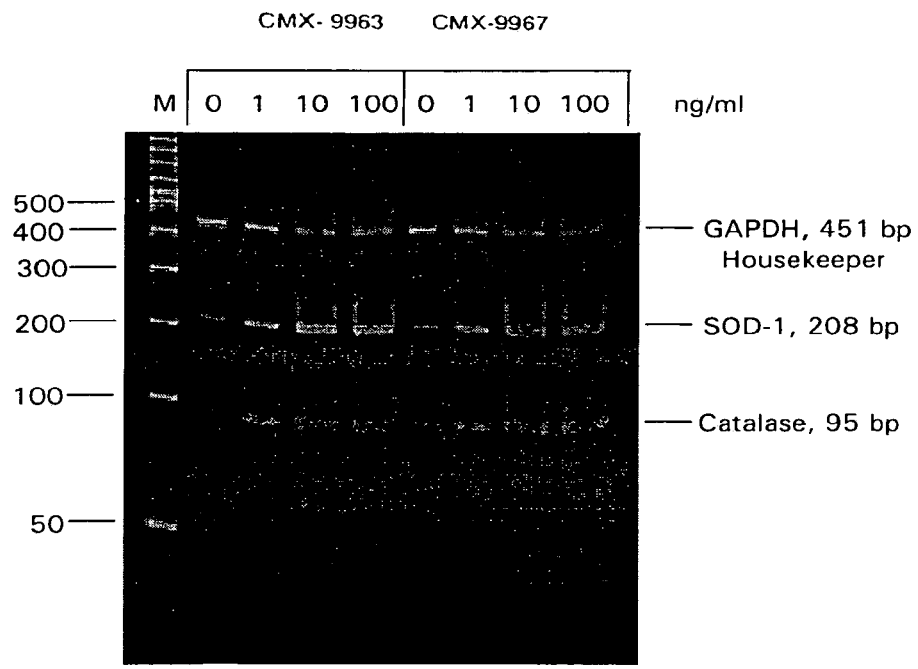
FIGS. 5A and 5B show that CMX-9963 and CMX-9967 upregulated mRNA transcripts for both SOD and catalase genes.
Figure 5B:
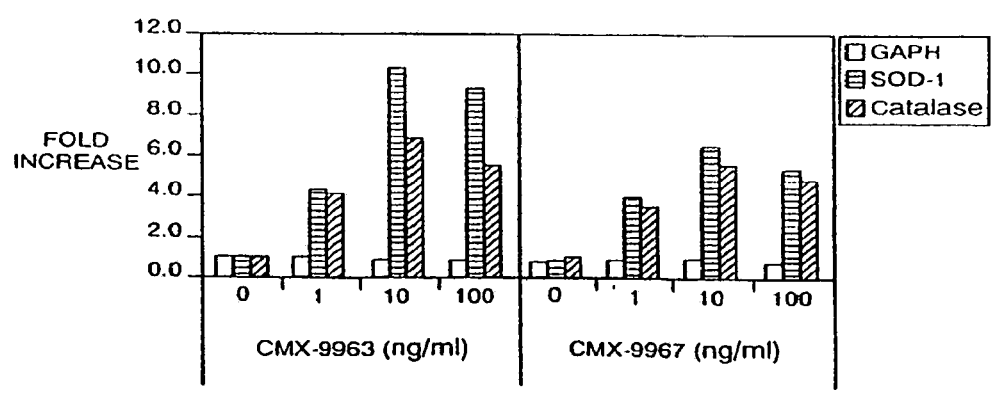

FIGS. 5A and 5B show results that demonstrate that other peptide compounds (i.e., CMX-9963 and CMX-9967) can also upregulate both CAT and SOD in primary rat cortical cultures. FIG. 5A shows a gel of RT-PCR products for cultures incubated for 3 hours with 0, 1, 10, and 100 ng/ml of CMX-9963 or CMX-9967. FIG. 5B shows bar graphs of the quantitative analysis data plotted as fold-increase as a function of dose for each peptide. The bar graphs in FIG. 5B show that rat primary cortical cells incubated with 10 ng/ml of CMX-9963 showed a maximum increase of around 10-fold and 7-fold for SOD-1 (black bars) and CAT mRNA (open bars), respectively, whereas cells incubated with CMX-9967 showed a maximum increase of 6-fold for both SOD and CAT at concentrations of 10 ng/ml. GAPDH was the internal standard. These findings establish that the CMX peptide compounds can promote the synthesis for two of the primary endogenous antioxidative enzymes that can defend cells from the powerful effects of ROS and free radicals.

Upregulation of SOD in Rat Fibroblasts by Peptide Compounds CMX-9963 and CMX-9967

Rat fibroblasts were isolated from lungs of rat embryos (E-21) and grown in culture as for culturing rat brain cortical cells as described above. After five days in culture, confluent monolayers of fibroblasts were obtained and used in dose-response studies with CMX-9963 or CMX-9967 in vehicle buffer (Hanks balanced salt solution ("HBSS", Life Technologies, Baltimore, Md.) containing 5% xylitol) at 0, 1, 5, 10, and 100 ng/ml. After incubation in the presence of peptide compound for 6 hours, cytoplasmic fractions were isolated from each culture.

Cytoplasmic proteins were isolated according to published methods (Adams et al., *J. Leukoc. Biol.*, 62: 865-873 (1997)). The cell cultures were washed once in phosphate buffer saline (PBS) containing 20 mM EDTA and then suspended in 250 µl of freshly prepared lysis buffer (20 mM Hepes, pH 7.9, 10 mM KCl, 300 mM NaCl, 1 mM $MgCl_2$, 0.1% Triton X-100 nonionic detergent, 20% glycerol, 0.5 mM dithiothreitol (DTT), freshly supplemented with inhibitors as described in Adams et al., *J. Biol. Chem.*, 77: 221-233 (2000)). The suspensions were then incubated for at least 10 minutes on ice to lyse cells and then centrifuged (14,000×g for 5 minutes at 4° C.) to pellet cell debris. The supernatant cytoplasmic fractions were removed and stored as aliquots at −80° C. for analysis. The protein concentrations of the cytoplasmic fraction varied within 2-6 µg/µl.

The cytoplasmic proteins were separated by SDS-PAGE using 5 µg/lane on the gels. The gels were processed for Western immunoblots basically as described by Adams et al. (*General Cellular Biochemistry*, 77: 221-233 (2000)) to measure upregulation of SOD. The Western blots were also analyzed by laser densitometry to quantify SOD protein upregulation. The control for this experiment was an identical culture flask which was treated with vehicle (buffer, no peptide compound).

Western blots showed that both CMX-9963 and CMX-9967 upregulated SOD gene expression in rat fibroblasts. In particular, incubation with 10 ng/ml of either CMX-9963 or CMX-9967 resulted in at least a 20-fold increase in (upregulation of) SOD gene expression in rat fibroblasts relative to untreated cells.

Example 3

Upregulation of AP-1 Transcription Factor in Mammalian Cells by Peptide Compounds Immediately prior to use, a 1.0 mg aliquot of a peptide compound was dissolved in 1.0 ml of 5% xylitol in HBSS (Hanks' Balanced Salt Solution, Hanks and Wallace, *Proc. Soc. Exp. Biol. Med.* 71:196 (1949)), the pH neutralized with 0.1 N NaOH, and the solution filter sterilized. Each peptide compound migrated as a single peak on HPLC column (C-18). The structure of each peptide compound was confirmed by amino acid analysis, and its molecular weight was verified by mass spectroscopy.

Nuclear extracts for electrophoretic mobility shift assays (EMSAs) were prepared as described previously (Adams et al., *J. Leukocyte Biol.*, 62: 865-873 (1997)) using $1.0$-$2.0 \times 10^7$ cells per sample. All buffers were freshly supplemented with dithiothreitol (DTT, 0.5 mM), protease inhibitors: PMSF (0.5 mM), chymostatin, peptstatin-A, aprotinin, antipain, leupeptin (each at 1 µg/ml), and phosphatase inhibitors: NaF (10 mM), $ZnCl_2$ (1 mM), sodium orthovanadate (1 mM), and sodium pyrophosphate (5 mM). Aliquots of the final dialyzates were stored at −80° C. and discarded after use.

NB2a cells ($1.0$-$2.0 \times 10^7$ per sample) were washed in 1×PBS, 20 mM EDTA, then resuspended in 250 µl of lysis buffer (20 mM HEPES, pH 7.9, 10 mM KCl, 300 mM NaCl, 1 mM $MgCl_2$, 0.1% Triton X-100, 20% glycerol) freshly supplemented with DTT and inhibitors as described above. Suspensions were incubated for at least 10 minutes on ice to lyse cells, then centrifuged (14,000×g, 5 minutes, 4° C.) to pellet cell debris. Supernatant aliquots were stored at −80° C. and discarded after a single use.

Electrophoretic Mobility Shift Assays (EMSAs)

AP-1 transcription factor activation was assayed using an electrophoretic mobility shift assay (EMSA), as described by Adams et al., *J. Leukoc. Biol.*, 62:865-873 (1997)). Cultures of primary rat neurons (Cornell-Bell et al., *Cell Calcium*, 12: 185-204 (1991)) were stimulated for 3 hours with various concentrations (0, 1, 10, 100 ng/ml) of peptide CMX-9236. Nuclear extracts prepared as described above were separated by gel electrophoresis on non-denaturing gels and subjected to the EMSA procedure. This EMSA used an AP-1 synthetic duplex probe (Angel, P., 1987, *Cell* 49:729-739) having the sequence 5'-CGCTTGATGACTCAGCCGGAA (SEQ ID NO:33) and its antisense copy (complement strand), which were end-labeled with $P^{32}$ using polynucleotide kinase and $(\gamma\text{-}P^{32})$-ATP. For the EMSA reaction, the labeled probe (0.5 pmol) was mixed with 3 µg of nuclear extract protein in a solution containing 10 mM Tris-HCl, pH 7.5, 50 mM NaCl, 1 mM EDTA, 1 mM dithiothreitol, 5% glycerol, 0.02% β-mercaptoethanol, and 1 µg of poly-dI/dC (Pharmacia). Reaction mixtures were incubated at 25° C. for 20 minutes to allow complete complex formation by the duplex with its appropriate AP-1 protein. The mixture was then electrophoresed under non-denaturing conditions through 4% polyacrylamide gels in 0.5×TBE buffer (45 mM Trisma base, 45 mM boric acid, 1 mM EDTA). The gels were dried on 3 mm paper. Bands were visualized by autoradiography at −80° C. with one intensifying screen and quantified by laser densitometry. The upregulation of AP-1 and the activation and upregulation process of AP-1 was compared to control cultures.

Figure 6A:
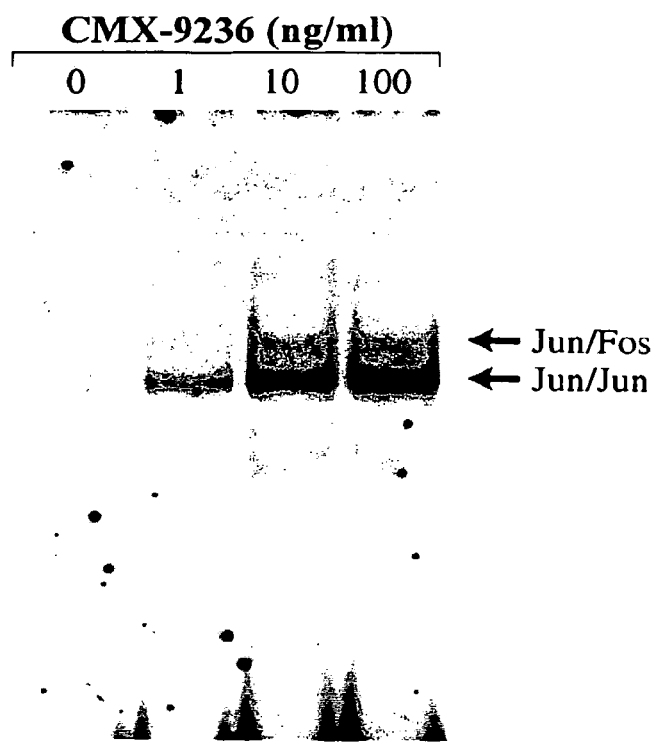
FIGS. 6A, 6B, and 6C show that CMX-9236 activated transcription factor AP-1 in primary rat cortical cultures stimulated for 3 hours with various concentrations (0, 1, 10, 100 ng/ml) of peptide compound CMX-9236.
Figure 6B:
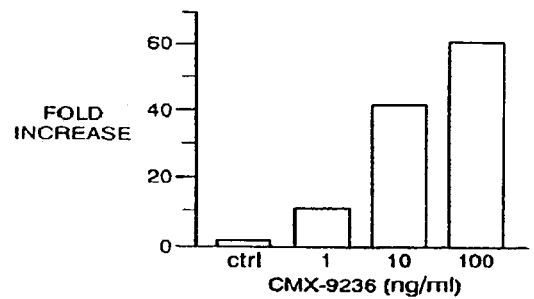

FIG. 6A shows the autoradiogram of a gel of the EMSA procedure for the primary rat neurons. Maximum upregulation was obtained when such cultures were incubated with 100 ng/ml of peptide compound CMX-9236. FIG. 6B shows a bar graph of the quantitative analysis of the data plotted as fold-increase as a function of dose of CMX-9236. The data indicate that there was a 60-fold increase in the binding of the DNA duplex probe at the position of the electrophoretic migration of the complexes formed with the DNA probe and the c-Jun/c-Fos heterodimer and the c-Jun/c-Jun homodimer forms of AP-1 in the gel; indicative of upregulation of AP-1 (see, FIGS. 6A and 6B).

Probe Competition EMSA

Figure 6C:
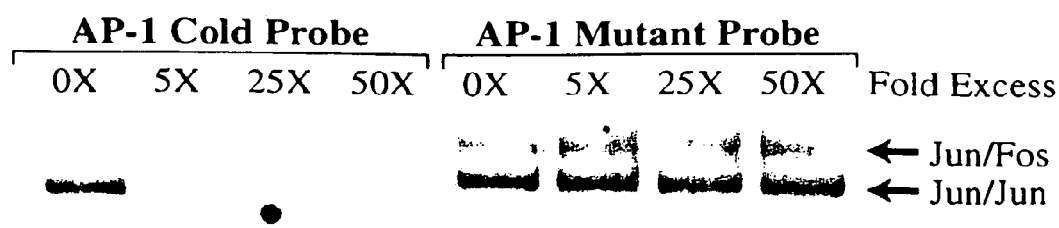

Probe competition EMSAs were carried out as in the EMSAs described above, except that a non-radiolabeled ("cold") duplex AP-1 oligomer (see above) or "cold" mutant AP-1 duplex oligomer comprising the nucleotide sequence CGCTTGATGACT<u>TG</u>GCCGGAA (mutant bases underlined, SEQ ID NO:34) and its complementary strand were added to the EMSA reactions and incubated for 20 minutes at 25° C. prior to addition of the $^{32}$P-labeled probe. Following radiolabeled probe addition, the incubation was continued at 25° C. for an additional 20 minutes prior to electrophoresis. The molar excess (0×, 5×, 25×, 50×) of cold probe relative to the 0.5 pmol of radiolabeled probe eliminated binding of the labeled duplex added to each electrophoretic lane. The cold mutant probe with mutations at the two underlined positions (TG) could not eliminate binding. This signifies that the probe had the correct sequence and a high degree of specificity for AP-1 (see, FIG. 6C).

Improved EMSAs may now be carried out basically as described above, except that an AP-1 synthetic duplex probe comprising the nucleotide sequence CGCTTGATGA GTCAGCCGGA A (SEQ ID NO:35) and its antisense copy (complement strand) are used for the standard assay and a mutant AP-1 duplex oligomer comprising the nucleotide sequence CGCTTGATGA GT<u>TG</u>GCCGGAA (mutant bases underlined, SEQ ID NO:36) and its complementary strand are used for the probe competition assay.

A number of investigations have demonstrated that both nerve growth factor (NGF) (Hsu et al., *Stroke*, 24 (suppl. I): I-78-I-79 (1993)) and brain derived neurotrophic factor (BDNF) (Schabitz et al., *J. Cereb. Blood Flow Metabol.*, 17: 500-506 (1997)), which are high molecular weight proteins than the peptide compounds described here, can stimulate neuronal growth by a mechanism that involves the activation (upregulation of expression) of the gene encoding transcription factor AP-1. The data indicate that the peptide compounds described herein also upregulate expression of the gene encoding AP-1 (see, FIGS. 6A, 6B, and 6C).

Primary cortical cell cultures were grown to confluence and used in in vitro cultures for determining the effects of various representative peptide compounds on upregulation of AP-1. Stimulation of AP-1 factor was found to increase in a dose-dependent manner, increasing by about 15-fold up to a maximum of 60-fold after a 3-hour incubation at 35.5° C. with 1, 10, or 100 ng/ml concentrations of the peptide (FIG. 6A). Extracts were prepared from the nuclei isolated from the primary culture homogenates, purified, and analyzed for the presence of specific transcription factors using the electrophoretic mobility shift assay (EMSA) method. The binding of $^{32}$P-labeled duplex DNA probes specific for activator protein-1 (AP-1) or nuclear factor κB (NF-κB) was analyzed and quantified by autoradiography. After a 3-hour incubation of the cultures with 1 ng/ml of the peptide CMX-9236 there was a 15-fold increase of AP-1 relative to stimulated control cultures. Incubations with 100 ng/ml of the peptide typically increased the level of AP-1 by 60-fold. This suggests that the peptide compounds described herein are able to affect the cascade of biochemical events that cause the phosphorylation of AP-1 and its translocation to the cell nuclei to increase c-Fos and the upregulation of AP-1-dependent gene expression. Thus, a small peptide compound that is less than 20 amino acids long can simulate the properties of large growth factors such as NGF and BDNF, which exist as dimers of protein chains with molecular weights of 13,259 and 13,500, respectively. The data suggest that the peptide compounds described herein are capable of activating genes that may be involved in brain cell growth. Such a mechanism has been previously demonstrated to block apoptosis, reversing programmed cell death in the nematode (Horvitz et al., *Cold Spring Harbor Symposium Quant. Biol.*, 111:377 (1994)) And Mammalian Nervous System (Yuan et al., *Cell* 75:641 (1993).

In control experiments (a negative control), the amino terminal capping group and blood-brain barrier transmigration facilitator DHA, alone, did not activate AP-1. However, peptide compounds without this DHA amino terminal capping group could activate AP-1 at an equivalent molar concentration to the DHA-coupled peptide compound. This indicates that the stimulation of AP-1 activity by the peptide compounds described herein depends on the peptide sequence.

The specificity of the interaction of the DNA probe with AP-1 was demonstrated in two additional types of control experiments. A 5-fold molar excess of non-radioactive AP-1 probe was found to completely block the formation of AP-1-$^{32}$P-DNA complex (see, FIG. 6C), while AP-1 with two errors in its sequence completely lost its capacity to form complexes even when used at a 50-fold molar excess relative to the radiolabeled probe (see, FIG. 6C). These results demonstrated a high degree of specificity of the AP-1 probe interaction and validated the EMSA assay.

The data indicate that the peptide compounds can activate AP-1 gene expression in neuronal cells. They demonstrate that a small peptide compound can have properties similar to those of a large neurotrophic protein factor, such as BDNF or NGF, which stimulate neuronal growth via activation of AP-1. Further evidence in support of such a concept is the finding that an inhibition of activation of AP-1 correlates with events that lead to neuronal cell death (Tabuchi et al., *J. Biol. Chem.*, 271: 31061-31067 (1996)). Upregulation of AP-1 seems to correlate with the process of cell growth, and its down-regulation seems to correlate with the process of cell death. In one other control experiment, peptide compounds did not promote the upregulation of the transcription factor NF-κB. This is a transcription factor that is associated with immune responses, i.e., not related to neuronal growth (Adams et al., *J. Leukoc. Biol.*, 62: 865-873 (1997)). Such a result has also been reported in literature for NGF, which is found to activate AP-1, but not NF-κB in PC12 cells (Tong and Perez-Polo, *J. Neurosci. Res.*, 45: 1-12 (1996)).

Example 4

In vivo Pharmacological Activity of Peptide Compounds CMX-9236, CMX-9236D, CMX-9967, and CMX-9902

The in vivo neuroprotective effects of CMX-9236 were investigated in both temporary and permanent occlusion stroke models in Sprague-Dawley rats using an intraluminal suture of the middle cerebral artery (MCA) occlusion method (Zea Longa et al., *Stroke*, 20: 84 (1989)). Briefly, a 4-0 silicone-coated suture was inserted through the right common carotid artery to block the MCA orifice. In the temporary model, CMX-9236 (6.2 mg/kg/hr) or vehicle was administered via the femoral vein at 30 minutes after the start of a 2-hour occlusion for a 4-hour continuous infusion; the rats were then reperfused by withdrawing the suture at 90 minutes after the MCA occlusion. All experiments were performed in a blinded and randomized manner, and rectal temperature was maintained at 37° C. The animals were sacrificed, and their brains were removed, sectioned into six 2-mm-thick coronal slices and stained with 2,3,5-triphenyltetrazolium chloride solution (Bederson et al., *Stroke*, 17:1304 (1986)) to visualize the extent of brain damage for the calculation of the corrected hemispheric infarct volumes (Nagasawa and Kogure, *Stroke*, 20:1037 (1989); Li et al., *J. Cereb. Blood Flow Metab.*, 17:1132 (1997)). In rats (n=10) treated with CMX-9236, the mean±S.E. for the corrected infarct volume was found to be 117.3±17 mm$^3$, as compared to 178.8±11 mm$^3$ for the vehicle-treated controls (n=10). This represents a significant reduction of infarct size (35±5%, p=0.01, student t-test) for the CMX-9236-treated group in the temporary occlusion model. There was also a 58+11% improvement in the neurological scoring (Minematsu et al., *Neurology*, 42:235 (1992)) for the peptide-treated group versus controls at the end of 24 hours.

In the permanent occlusion stroke model, the blood flow to the MCA territory was blocked for the total 24-hour period. A continuous i.v. infusion (0.5 ml/hr) of the CMX-9236 peptide (2.04 mg/kg/hr) or vehicle was initiated at 30 minutes after occlusion for 6 hours, followed by a bolus i.v. infusion of CMX-9236 (4.0 mg/kg in 0.5 ml delivered over 10 minutes) or vehicle at 12 hours after occlusion. The corrected infarct volumes were 127.5±18 mm$^3$ versus 216±18 mm$^3$ for drug-treated animals and controls, respectively. This represents a significant decrease (41±5%, p=0.003, student t-test) in infarct size for the drug-treated group as compared to the vehicle-treated control group (n=10 per group) in the permanent model, indicating a substantial rescue of brain tissue.

These findings indicate that CMX-9236 has neuroprotective properties post-trauma in vivo, reducing the brain damage generated by cerebral ischemia. Table 2 shows the results for different CMX peptides using the MCA permanent occlusion test.

TABLE 2

Effects of CMX Peptides on Infarct Size and Neurological Behavior of Rats Using the Permanent MCA 24-Hour Occlusion Method

| Compound | Dose (mg/hr) | n | Percent Rescue[a] | Percent Neurological Rescue |
|---|---|---|---|---|
| CMX-9236D (DHA-capped peptide) | 0.03 | 7 | 48 ± 12 | 50 ± 18 |
| CMX-9236 (uncapped peptide) | 0.05 | 4 | 23 ± 7 | 35 ± 8 |
| CMX-9967 | 0.05 | 4 | 20 ± 6 | 40 ± 10 |
| CMX-9902 | 0.05 | 8 | 29 ± 7 | 35 ± 12 |

[a]Percent rescue denotes the percent decrease in infarct size in comparison to identical treatment of controls (n = 8) with vehicle alone.

Example 5

Activities of Other Representative Peptide Compounds

Certain activities have been demonstrated for other representative peptide compounds using one or more the assays described in the proceeding Examples. CMX-9901 and CMX-8933 peptide compounds upregulated AP-1 and provided a positive neuroprotective effect in the in vivo permanent MCA assay. CMX-9902 upregulated SOD proteins and increased nuclear migration of AP-1 in culture in vitro studies.

Example 6

In vivo and In vitro Pharmacological Activity of Related Dipeptide Compounds CMX-1152 (Asp Gly) and CMX-99672 (TPA Salt of Asp Gly)

In vivo experiments were carried out in Sprague-Dawley rats (300-325 g) with solutions of CMX-1152 or CMX-99672. The animals were injected intravenously (iv) via the tail vein with a peptide compound. Each animal received three injections, one hour apart (i.e., 0.3 ml of the peptide compound at a concentration of 10 μg/ml in normal saline for a total dose equivalent to 9 mg peptide compound/kg body weight. The animals were sacrificed by decapitation at 6, 12, 24, 48, and 72 hours post injection and dissected to isolate brain, liver, heart, kidney, lung organs, which were frozen at −70° C. for subsequent analysis. In addition, 2 ml samples of whole blood were taken from each animal. Half (1 ml) of each sample was centrifuged to remove nuclei and cell membranes to yield plasma. The remaining half was stored frozen as whole blood at −70° C.

Western Immunoblots Using Antiserum to Human SOD and CAT Enzymes

Each tissue was thawed and homogenized in a Down's homogenizer using ten volumes of homogenizer buffer (see, Adams et al., *General Cellular Biochemistry*, 77: 221-233 (2000); buffer as described in Adams et al., *J. Leukoc. Biol.*, 62: 865-875 (1967)) to obtain a crude cytoplasmic fraction. The tissue homogenates were centrifuged (14,000×g for 5 minutes at 4° C.) to yield the supernatant purified cytoplasmic protein fractions as described in Adams et al. (*J. Cell. Biochem.*, 77: 221-233 (2000)). A 10 µg sample of each protein fraction was then separated by SDS polyacrylamide gel electrophoresis (SDS-PAGE) and analyzed for SOD and CAT content by Western blot assay.

Control for measurement of unstimulated levels of SOD and CAT were obtained from two vehicle only (i.e., no peptide compound) injected rats that were sacrificed at 24 and 72 hours post injection. Both had essentially the same unstimulated levels of SOD and CAT. Standard quantities of each cytoplasmic fractions (10 µg) were loaded on a lane of a gel for electrophoretic separation and Western immunoblot analysis (Adams et al., *J. Cell. Biochem.*, 77: 221-233 (2000)). The stained gels were photographed and scanned by laser densitometry to quantify intensities in comparison to enzyme levels for control vehicle treated rats.

Table 3 shows the upregulation data for SOD in various rat organs compared to control animals that received only the injection vehicle without peptide compound. The data show that administration of the peptide compound CMX-1152 resulted in approximately a four to five-fold upregulation in SOD production in brain, heart, lung, and blood relative to the control, and an approximately two-fold upregulation in SOD production in liver and kidney. These results indicate that the peptide compound CMX-1152 is active in vivo and that it is active in every major tissue and organ. Thus, the peptide compound CMX-1152 can upregulate SOD in whole animals. Similar results were obtained for CAT (data not shown). These findings demonstrate the potential of CMX-1152 for use as a treatment that promotes the defense of the whole organism against ROS and free radicals. Accordingly, the body-wide, substantial antioxidative activity generated by the peptide compound CMX-1152 qualifies this peptide compound as a particularly, well suited anti-aging candidate compound that may be developed for use as a "healthy life expectancy" drug.

TABLE 3

In Vivo Upregulation of Superoxide Dismutase (SOD) in Sprague-Dawley Rats After a 6-Hour Treatment with CMX-1152 at a Dose of 10 mg/kg

| Organ | SOD Activity (% of Control*) |
| --- | --- |
| Brain | 520 |
| Heart | 550 |
| Liver | 200 |
| Lung | 520 |
| Kidney | 200 |
| Plasma | 420 |
| Whole Blood | 490 |

*Control levels = 100%; injection of normal saline (vehicle)

Additionally, studies of the time course of the in vivo upregulation of SOD and CAT by administration of the peptide compound CMX-1152 persisted for a substantially longer period in tissues than in tissue not exposed to CMX-1152. The in vivo data given in Table 3 compare SOD levels for CMX-1152 versus vehicle (saline) treated controls. The control values for each tissue remained constant as a function of time.

Additional Studies of CMX-1152 and CMX-99672

CMX-99672 and CMX-1152 peptide compounds comprise the same Asp-Gly dipeptide. CMX-99672 is the trifluoracetic acid salt form and CMX-1152 is the acetate salt form of the dipeptide. In this study, CMX-99672 was only used in the describe in vitro tissue culture experiments, whereas CMX-1152, as a purified acetate salt form that is free of trifluoroacetic acid, was used in all in vivo experiments.

Tissue culture experiments were carried out using primary cultures of rat brain cortical cells as previously described above in Example 2. Primary cultures from embryonic rat brain isolated at E-21 (21 day embryos) and incubated for five hours with various doses: 1, 10, 100 ng/ml of CMX-99672. Cytoplasmic proteins were isolated and analyzed for upregulation of SOD and CAT by Western immunoblots as described above. Western blots showed upregulation of SOD and SOD-related protein by CMX-99672. The Western blot was scanned to quantify the fold-increase in SOD production in cell cultures treated with the CMX-99672 peptide compound. Exposure to CMX-99672 resulted in an approximately 30-fold increase in SOD and 20-fold increase in SOD-related protein. Comparable data was obtained for CAT.

These data indicate that the dipeptide Asp-Gly is highly effective at substantially increasing the anti-oxidative activity in cells and tissues of a mammal, and especially in the cells and tissues of the central nervous system. Again, such data indicate that this simple Asp-Gly dipeptide compound is a candidate compound for use in compositions and methods to counteract the effects of ROS and other free radicals, whether generated by the aging process, disease, or drug treatments.

Example 7

In vitro Study of Peptide Compounds CMX-99658 and CMX-8933

Two other peptide compounds CMX-99658 ([Ac]-Gln Thr Leu Gln Phe Arg) (SEQ ID NO:2), and CMX-8933 (Lys Lys Glu Thr Leu Gln Phe Arg) (SEQ ID NO:24) (described in U.S. Pat. No. 5,545,719). The essential difference between these two compounds is not presence of the particular protective amino terminal capping group (i.e., acetyl or Lys Lys), but the presence of the first amino terminal glutamine or glutamic acid in the core peptide sequence. The two peptide compounds were tested for the ability to upregulate SOD and CAT in rat primary cortical cells. Rat primary cortical cells were isolated from E-21 rat embryos as described above in Example 4, except the cells were incubated with CMX-99658 or CMX-8933 at 0.7, 7, and 70 ng/ml. Cells were incubated for 6 hours with a peptide or with a control medium containing no peptide. SOD and CAT levels were analyzed by Western immunoblot using commercially available antibodies to detect SOD and CAT (Rockland, Inc., Gilbertsville, Pa.).

The data indicated that CMX-8933 and peptide compounds comprising the Glu Thr Leu Gln Phe Mg (SEQ ID NO:13) amino acid sequence are preferred in various methods of the invention that rely upon the upregulation of SOD and/or CAT gene expression to provide the levels of antioxidative enzyme activities to counteract the generation of ROS and other free radicals (e.g., due to aging, drug treatment, and disease).

Example 8

Upregulation of SOD and CAT in Rat Primary Cortical Cultures by Other Representative Peptide Compounds Representative peptide compounds were tested at various doses and compared for their ability to upregulate expression of genes for SOD and/or CAT in rat primary cortical cultures basically as described above. Cultures were incubated with a peptide compound for 5 hours at 37° C. Cytoplasmic protein fractions were prepared as described above. Cytoplasmic proteins were separated by gel electrophoresis and analyzed by Western immunoblots using antisera to SOD and CAT, respectively (Rockland, Inc., Gilbertsville, Pa.). The results are shown in Table 4 (below).

TABLE 4

Upregulation of SOD and CAT by Peptide Compounds in Rat Primary Cortical Cultures

| Peptide (CMX designation) | Dose (pmol/ml) | SOD (% Control) | CAT (% Control) |
|---|---|---|---|
| None (Control) | 0 | 100 | 100 |
| Asp Gly (CMX-1152) | 6.7 | 2143 | N.D. |
| [Ac] Asp Gly Asp (CMX-9967) | 28 | 1220 | 200 |
| [Ac] Thr Val Ser (CMX-99647) | 6.7 | 2066 | N.D. |
| [Gga] Asp Gly Asp Gly Phe Ala (CMX-99661) (SEQ ID NO: 5) | 6.7 | 463 | N.D. |
| [Ac] Asp Gly Asp Gly Phe Ala (CMX-99655) (SEQ ID NO: 5) | 8 | 750 | 520 |
| [Palm] Asp Gly Asp Gly Phe Ala (CMX-9960) (SEQ ID NO: 5) | 6.7 | 527 | N.D. |
| [Ac] Asp Gly Asp Gly Asp Phe Ala (CMX-9963) (SEQ ID NO: 6) | 6.7<br>28 | 1873<br>N.D. | N.D.<br>700 |
| Lys Lys Gln Thr Leu Gln Phe Arg (SEQ ID NO: 25) | 95 | 350 | 400 |
| Lys Lys Asp Gly Asp Gly Asp Phe Ala Ile Asp Ala Pro Glu (CMX-9236) (SEQ ID NO: 26) | 6.7<br>67 | 466<br>N.D. | N.D.<br>652 |

Control = normal saline;
SOD = superoxide dismutase;
CAT = catalase;
[Ac] = acetyl;
[Gga] = 3-O-glucose-glycolic acid;
[Palm] = palmitoyl;
N.D. = not determined The above data demonstrate that the peptides are capable of upregulating antioxidative enzymes, i.e., SOD and/or CAT. Peptide compounds comprising the amino acid sequence Asp Gly Asp Gly Phe Ala (SEQ ID NO:5) were able to upregulate both SOD and CAT to essentially equal levels. Such equipotent activity for upregulating both SOD and CAT indicates that this peptide is particularly preferred for providing adequate relative levels of the complementary antioxidative enzyme activities of SOD and CAT to counteract oxidative stress produced from a variety of sources and conditions, as well as to effectively detoxify hydrogen peroxide generated by SOD activity on super oxide anions.

Example 9

Preparation of an Active Fraction from Green Velvet Antler (Gva) and Formulation of Nutraceutical Compositions from an Animal Source Natural Source Purification, Analysis, and Formulation of Nutraceutical Compositions Five grams of the raw GVA dry powder from Qeva, Inc. (Calgary, Ontario, Canada), were extracted with 100 ml of water at room temperature for 30 minutes. The water soluble components ("GVAW") were then separated from the insoluble residue by centrifugation for 30 minutes at 5,000×g. The residue was further extracted by re-suspension in 50 ml of water and stirring for additional 30 minutes. The mixture was then re-centrifuged (30 minutes at 5,000×g) and the supernatants from the two extracts were combined to give a crude yellow extract. This was re-centrifuged at 10,000×g for 30 minutes at room temperature. The supernatant fraction was removed and sterilized by filtration through a Millipore filter (0.2 μm pore size) to give a clear yellow solution. This clear yellow solution was then concentrated to 10-20 ml in a rotary evaporator at 30° C. under mild vacuum, and lyophilized to give the fraction GVAW as a brown, fluffy powder (yield 15-20%). This fraction contains an active peptide that can up-regulate SOD (see Table 5) in primary rat brain cortical cultures as described above.

Additional purification of the GVAW fraction was carried out by column chromatography using Biogel (PD-10) from Bio-Rad Laboratories (Hercules, Calif. 94547). This separated the peptides with a molecular weight (MW) higher than 6,000 daltons from those with a MW of less than 6,000 daltons to give two fractions: GVA +6 and GVA −6, respectively, and to give yields (based on raw material) of lyophilized products of 8-10% and 3-6%, respectively.

GVA −6 contained a concentrate of an active GVA peptide. Analysis by thin layer chromatography on silica gel flexible sheets (J. T. Baker Inc., Phillipsturg, N.J.) using ethanol/ammonium hydroxide (70/30) as the eluant showed the presence of many peptide components that included one that had identical migration properties to CMX-1152 (Asp Gly). Additional confirmation was obtained by mass spectroscopy that showed the presence of two components that have MWs of 236 and 190 corresponding to the disodium salt and the free acid form of Asp Gly, respectively. Amino acid analysis of the GVA −6 fraction showed the presence of the amino acids Asp and Gly in equimolar amounts in the mixture. GVA −6 also had the property of up-regulating SOD in rat brain primary cortical cultures. It was at least 3,000 times more active than the GVA +6 fraction (see Table 5, below).

TABLE 5

| Fraction | Dose (ng/ml) | SOD Upregulation (% Control) |
|---|---|---|
| Control | — | 100 |
| GVAW | 100 | 250 |
| GVA − 6 | 10 | 220 |
| GVA − 6 | 100 | 330 |
| GVA + 6 | 100 | 105 |
| GVA + 6 | 1000 | 132 |
| DG (CMX-1152) | 1 | 170 |
| DG | 10 | 330 |
| DG | 100 | 420 |

Both GVAW and GVA −6 fraction were augmented with pure synthetic Asp Gly peptide to obtain a therapeutic level of SOD up-regulation properties in a standard assay using rat brain primary cultures. Typical formulations will have the necessary amount of CMX-1152 to obtain an approximately 1.3 to 10.0-fold up-regulation of SOD in plasma and blood samples.

Alternative Method of Preparing GVA –6 Fraction

The column chromatography step in the above method was replaced by direct extraction of GVAW fraction with 100% methanol. Here the high molecular weight components formed a precipitate, which was then separated to yield clear filtrate which, after treatment with active charcoal, produced a colorless solution. The colorless solution yielded a white solid after lyophilization. This had a similar composition to that of GVA –6 described above.

Example 10

Preparation of an Active Fraction from a Plant Source and Formulation of Nutraceutical Compositions Similar methods as described in Example 9 were used to obtain an active fraction from Wu, Zi, Yan, Zong, Wan herbal mixtures (see, e.g., Wang et al., *Chung Kuo Chung His I Chieh Ho Tsa Chih* 12: 23-25 (1992), study of wuzi yanzong liquid; Huang et al., *Chung Kuo Chung Yao Tsa Chih* 16: 414-416, 447 (1991), study of fufang wuzi yanzong pills) to obtain formulations that have a standard level of SOD up-regulation properties. Typical formulations for nutraceutical compositions will be converted to a standard potency level by adding pure synthetic CMX-1152 to obtain SOD up-regulation of approximately 1.3 to 10-fold up-regulation of SOD in plasma and blood samples.

Various amino acid and nucleotide sequences referred to herein and their corresponding sequence identification numbers (SEQ ID NO:) are listed in Table 6, below. Variable amino acids (Xaa) present in some these sequences are described in more detail above.

TABLE 6

Sequences and Corresponding Sequence Identification Numbers

| Sequence | Sequence Identification Number |
|---|---|
| Gln Tyr Lys Leu Gly Ser Lys Thr Gly Pro Gly Gln | SEQ ID NO: 1 |
| Gln Thr Leu Gln Phe Arg | SEQ ID NO: 2 |
| Xaa₁ Gly Xaa₂ Xaa₃ Xaa₄ Xaa₅ Xaa₆ | SEQ ID NO: 3 |
| Asp Gly Asp Gly Asp | SEQ ID NO: 4 |
| Asp Gly Asp Gly Phe Ala | SEQ ID NO: 5 |
| Asp Gly Asp Gly Asp Phe Ala | SEQ ID NO: 6 |
| Asp Gly Asn Gly Asp Phe Ala | SEQ ID NO: 7 |
| Asn Gly Asn Gly Asp Phe Ala | SEQ ID NO: 8 |
| Asn Gly Asp Gly Asp Phe Ala | SEQ ID NO: 9 |
| Xaa₁ Xaa₂ Met Thr Leu Thr Gln Pro | SEQ ID NO: 10 |
| Met Thr Leu Thr Gln Pro | SEQ ID NO: 11 |
| Ser Lys Met Thr Leu Thr Gln Pro | SEQ ID NO: 12 |

TABLE 6-continued

Sequences and Corresponding Sequence Identification Numbers

| Sequence | Sequence Identification Number |
|---|---|
| Glu Thr Leu Gln Phe Arg | SEQ ID NO: 13 |
| Gln Tyr Ser Ile Gly Gly Pro Gln | SEQ ID NO: 14 |
| Ser Asp Arg Ser Ala Arg Ser Tyr | SEQ ID NO: 15 |
| Asp Gly Asp Gly Asp Phe Ala Ile Asp Ala Pro Glu | SEQ ID NO: 16 |
| Asn Gly Asn Gly Asp | SEQ ID NO: 17 |
| Asp Gly Asn Gly Asp | SEQ ID NO: 18 |
| Asn Gly Asp Gly Asp | SEQ ID NO: 19 |
| Asn Gly Asp Gly | SEQ ID NO: 20 |
| Asn Gly Asn Gly Phe Ala | SEQ ID NO: 21 |
| Asp Gly Asn Gly Phe Ala | SEQ ID NO: 22 |
| Asn Gly Asp Gly Phe Ala | SEQ ID NO: 23 |
| Lys Lys Glu Thr Leu Gln Phe Arg | SEQ ID NO: 24 |
| Lys Lys Gln Thr Leu Gln Phe Arg | SEQ ID NO: 25 |
| Lys Lys Asp Gly Asp Gly Asp Phe Ala Ile Asp Ala Pro Glu | SEQ ID NO: 26 |
| Lys Lys Gln Tyr Lys Leu Gly Ser Lys Thr Gly Pro Gly Gln | SEQ ID NO: 27 |
| Lys Lys Asp Gly Asp Gly Asp Phe Ala | SEQ ID NO: 28 |
| ATCCCAATCACTCCACAGGCCAAGC | SEQ ID NO: 29 |
| GAGACCTGGGCAATGTGACTGCTGG | SEQ ID NO: 30 |
| GCCCGAGTCCAGGCTCTTCTGGACC | SEQ ID NO: 31 |
| TTGGCAGCTATGTGAGAGCCGGCCT | SEQ ID NO: 32 |
| CGCTTGATGACTCAGCCGGAA | SEQ ID NO: 33 |
| CGCTTGATGACTTGGCCGGAA | SEQ ID NO: 34 |
| CGCTTGATGAGTCAGCCGGAA | SEQ ID NO: 35 |
| CGCTTGATGAGTTGGCCGGAA | SEQ ID NO: 36 |

Other variations and embodiments of the invention described herein will now be apparent to those of ordinary skill in the art without departing from the scope of the invention or the spirit of the claims below.

All patents, applications, and publications cited in the above text are incorporated herein by reference.

What is claimed is:

1. A method of treating an ischemic injury in a subject, the method comprising administering to the subject a peptide compound, wherein the amino acid sequence of the peptide compound is Asp Gly Asp, Asp Gly, Thr Val Ser, or Glu Ala, wherein the peptide compound is administered in an amount effective to treat the ischemic injury, wherein the peptide compound comprises an amino terminal capping group and/or a carboxy terminal capping group.

2. The method of claim 1, wherein the amino terminal capping group is a lipoic acid moiety (Lip).

3. The method of claim 1, wherein the ischemic injury is a reperfusion injury.

4. The method of claim 1 wherein the ischemic injury results from a stroke.

5. The method of claim 1, wherein the ischemic injury is a myocardial infarction.

6. The method of claim 1, wherein the ischemic injury results from an occlusion.

7. The method of claim 1, wherein the ischemic injury results from a heart attack.

8. The method of claim 1, wherein the ischemic injury is a drug-induced injury.

9. The method of claim 2, wherein the peptide compound is [Lip]-Asp Gly.

10. The method of claim 2, wherein the peptide compound is [Lip]-Glu Ala.

11. The method of claim 2, wherein the peptide compound is [Lip]-Asp Gly Asp.

12. The method of claim 2, wherein the peptide compound is [Lip]-Thr Val Ser.

13. A method for reducing an elevated level of reactive oxygen species (ROS) and/or free radicals in a subject, the method comprising administering to the subject a peptide compound, wherein the amino acid sequence of the peptide compound is Asp Gly Asp, Asp Gly, Thr Val Ser, or Glu Ala, wherein the peptide compound is administered in an amount effective to reduce the elevated level of ROS and/or free radicals in the subject, wherein the peptide compound comprises an amino terminal capping group and/or a carboxy terminal capping group.

14. The method of claim 13, wherein the elevated level of ROS and/or free radicals is the result of an ischemic injury in the subject.

15. A method for treating an ischemic injury in a subject, the method comprising administering to the subject a peptide compound, wherein the amino acid sequence of the peptide compound is Glu Gly, Asp Gly Asp Gly Asp, Asp Ala (SEQ ID NO:4), or Asp Gly Asp Gly Asp Phe Ala (SEQ ID NO:6), wherein the peptide compound is administered in an amount effective to treat the ischemic injury in the subject, wherein the peptide compound comprises an amino terminal capping group and/or a carboxy terminal capping group.

16. A method for reducing an elevated level of reactive oxygen species (ROS) and/or free radicals in a subject, the method comprising administering to the subject a peptide compound, wherein the amino acid sequence of the peptide compound is Glu Gly, Asp Gly Asp Gly Asp (SEQ ID NO:4), Asp Ala, or Asp Gly Asp Gly Asp Phe Ala (SEQ ID NO:6), wherein the peptide compound is administered in an amount effective to reduce the elevated level of ROS and/or free radical in the subject, wherein the peptide compound comprises an amino terminal capping group and/or a carboxy terminal capping group.

17. A method for treating an ischemic injury in a subject, the method comprising administering to the subject a peptide compound that has the formula:

R1 Xaa1 Xaa2 Xaa3 R2, wherein Xaa1 is Asp, Asn, Glu, Gln, Thr, or Tyr; Xaa2 is absent or any amino acid; Xaa3 is Asp, Asn, Glu, Thr, Ser, Gly, or Leu; R1 is absent or is an amino terminal capping group; R2 is absent or is a carboxy terminal capping group, and wherein the peptide compound comprises an amino terminal capping group and/or a carboxy terminal capping group.

18. A method for reducing an elevated level of reactive oxygen species (ROS) and/or free radicals in a subject, the method comprising administering to the subject a peptide compound that has the formula:

R1 Xaa1 Xaa2 Xaa3 R2, wherein Xaa1 is Asp, Asn, Glu, Gln, Thr, or Tyr; Xaa2 is absent or any amino acid; Xaa3 is Asp, Asn, Glu, Thr, Ser, Gly, or Leu; R1 is absent or is an amino terminal capping group; R2 is absent or is a carboxy terminal capping group, and wherein the peptide compound comprises an amino terminal capping group and/or a carboxy terminal capping group.

* * * * *